(12) United States Patent  (10) Patent No.: US 8,059,880 B2
Mizuta et al.  (45) Date of Patent: Nov. 15, 2011

(54) NUCLEAR MEDICINE DIAGNOSIS DEVICE, FORM TOMOGRAPHY DIAGNOSIS DEVICE, NUCLEAR MEDICINE DATA ARITHMETIC PROCESSING METHOD, AND FORM TOMOGRAM ARITHMETIC PROCESSING METHOD

(75) Inventors: Tetsuro Mizuta, Ritto (JP); Keishi Kitamura, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 500 days.

(21) Appl. No.: 12/344,417

(22) Filed: Dec. 26, 2008

(65) Prior Publication Data

US 2009/0169082 A1  Jul. 2, 2009

(30) Foreign Application Priority Data

Dec. 28, 2007 (JP) ................ 2007-338768
Dec. 25, 2008 (JP) ................ 2008-329410

(51) Int. Cl.
*G01T 1/161* (2006.01)
*G01T 1/164* (2006.01)
*G01T 1/166* (2006.01)
*G06K 9/00* (2006.01)

(52) U.S. Cl. ............... 382/131; 382/128; 250/363.04
(58) Field of Classification Search .......... 382/128–134; 250/363.04
See application file for complete search history.

(56) References Cited

U.S. PATENT DOCUMENTS

2006/0067578 A1 * 3/2006 Fuse ..................... 382/190

FOREIGN PATENT DOCUMENTS

JP  07-113873 A  5/1995
JP  2000-028727 A  1/2000

OTHER PUBLICATIONS

Knoess, Christof et al., "Development of a Daily Quality Check Procedure for the High-Resolution Research Tomograph (HRRT) Using Natural LSO Background Radioactivity", IEEE Transactions on Nuclear Science, vol. 49, No. 5, Oct. 2002, pp. 2074-2078.
Yamamoto, Seiichi et al., "Investigation of single, random, and true counts from natural radioactivity in LSO-based clinical PET", Annals of Nuclear Medicine, vol. 19, No. 2, 2005, pp. 109-114.
Goertzen, Andrew L. et al., "On the Imaging of Very Weak Sources in an LSO PET Scanner", IEEE Nuclear Science Symposium Conference Record, 2006, pp. 2323-2327.

* cited by examiner

*Primary Examiner* — David Mis
(74) *Attorney, Agent, or Firm* — Cheng Law Group, PLLC

(57) ABSTRACT

In a state in which a subject is absent, blank data is collected by a self-radioactivity element typified by Lu-176 (S1). In a state in which the subject is present, transmission data is collected by the self-radioactivity element (S2). Emission data is collected by γ rays emitted from the subject injected with a radiopharmaceutical (S3). Absorption-corrected data is calculated based on the blank data and the transmission data (S4 to S7), and the emission data is absorption-corrected using the absorption-corrected data (S8). Although such background data obtained by the self-radioactivity is originally abandoned, the background data is rather used for the absorption-corrected data. Stable absorption correction can be thereby conducted.

34 Claims, 12 Drawing Sheets

Fig.3
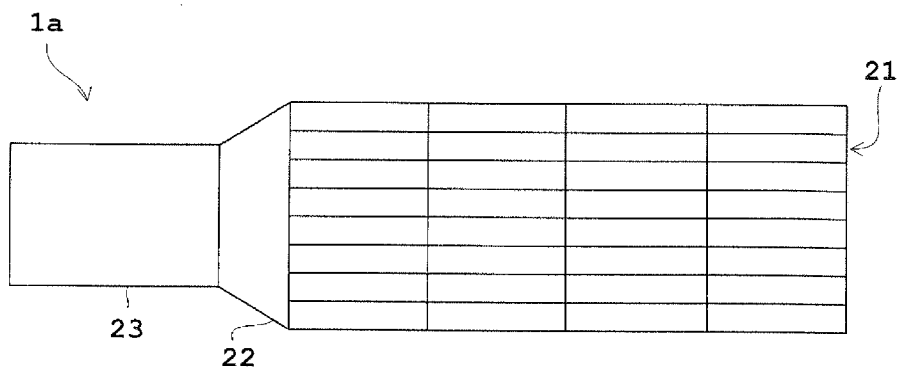
Fig.4A                    Fig.4B
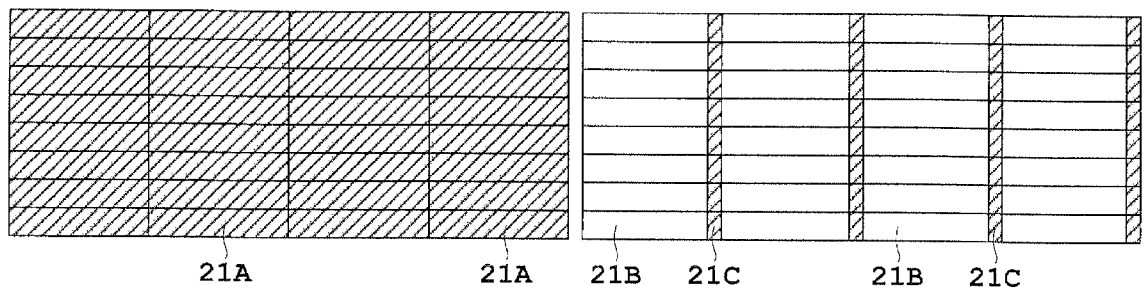

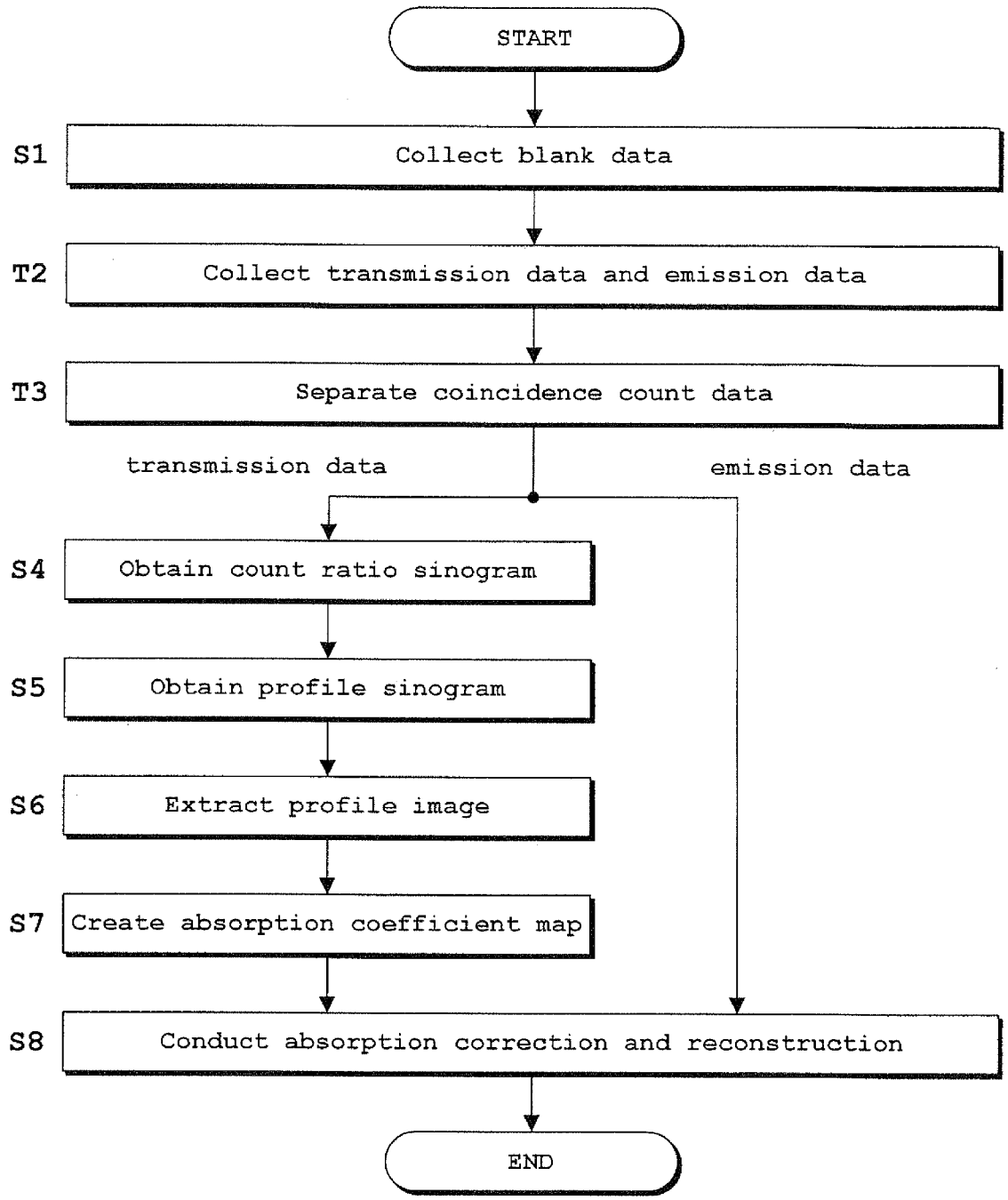

A1:E+T

B1:E

A1:E+T

B1:E

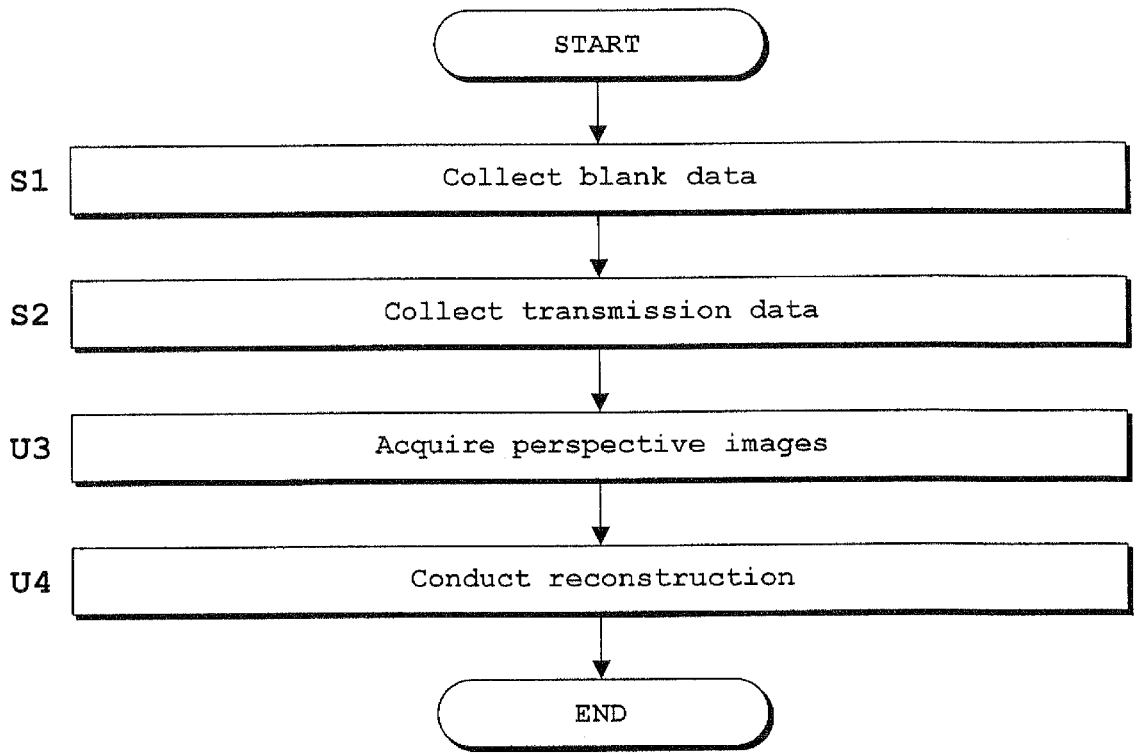

NUCLEAR MEDICINE DIAGNOSIS DEVICE, FORM TOMOGRAPHY DIAGNOSIS DEVICE, NUCLEAR MEDICINE DATA ARITHMETIC PROCESSING METHOD, AND FORM TOMOGRAM ARITHMETIC PROCESSING METHOD

BACKGROUND OF THE INVENTION (1) Field of the Invention

The present invention relates to a nuclear medicine diagnosis device, a form tomography diagnosis device, a nuclear medicine data arithmetic processing method, and a form tomogram arithmetic processing method for obtaining nuclear medicine data or form tomograms of a subject injected with radiopharmaceutical based on radiant rays generated from the subject.

(2) Description of the Related Art

The nuclear medicine diagnosis device, that is, an ECT (Emission Computed Tomography) device will be described while taking a PET (Positron Emission Tomography) device as an example. The PET device is configured to detect a plurality of gamma ($\gamma$) rays generated as a result of annihilation of positrons and to reconstruct tomograms of a subject only when a plurality of detectors detects the $\gamma$ rays simultaneously.

Specifically, a radiopharmaceutical containing a positron-emitting radionuclide is administered into the subject and detectors each constituted by many detector components (such as scintillators) detect pair annihilation $\gamma$ rays of 511 KeV emitted from within the subject injected with the radiopharmaceutical. If the two detectors detect $\gamma$ rays in certain time, it is assumed that the detectors detect $\gamma$ rays simultaneously. The detected $\gamma$ rays are calculated as pairs of pair annihilation $\gamma$ rays and a pair annihilation generation point is identified to be on a line of each pair of detectors detecting the $\gamma$ rays. By accumulating such coincidence count information and performing a reconstruction processing, positron-emitting radionuclide distribution images (that is, tomograms) is obtained. The technique is disclosed in, for example, Japanese Patent Application Laid-Open Nos. 7-113873 and 2000-28727.

To keep quantitative performance and imaging quality high in the nuclear medicine diagnosis, it is essential to absorb and correct the coincidence count information data (also referred to as "emission data"). Absorption of the coincidence counting data by the PET device depends on a path on which the $\gamma$ rays pass through the subject and does not depend on $\gamma$ ray generation points (positron pair annihilation generation points). Normally, therefore, an external radiant source irradiating radiant rays of the same type ($\gamma$ rays in this case) as that of the radiopharmaceutical is employed. An inverse of a transmission factor or an absorption correction value obtained from an absorption coefficient map is multiplied by emission projection data, whereby form information (also referred to as "transmission data") based on the $\gamma$ rays irradiated from the external radiant source and transmitted by the subject can be absorption-corrected. Recently, a technique for converting form information obtained from an X-ray CT device integrated with a PET device (PET-CT device) in place of the external radiant source into an absorption coefficient map and for using the absorption coefficient map for absorption correction has been adopted.

However, if it is difficult to mount the external radiant source or the like and an interior of the subject can be assumed as a uniform absorber, a technique for estimating a contour of the subject from the emission data or images, assuming the interior as a uniform absorber and performing absorption correction on the uniform absorber is adopted. This technique is disclosed in, for example, KITAMURA Keiji, ISHIKAWA Yoshihiro, MIZUTA Tetsuro, YOSHIDA Eiji and YAMAYA Taiga: "Development of Various Data Correction Method in jPET-D4", Next-generation PET Device Research and Development Report 2005, pp. 47 to 51.

Recently, particularly in development of high resolution PET, scintillators (LSO, LYSO, LGSO, etc.) including Lu-176 have been often used as the scintillators constituting each detector in light of a high emission amount, short luminescent decay time and high $\gamma$ ray blocking capability during conversion of radiant rays into light by the scintillators. These characteristics are the basis for and have influence on performances of the PET device, that is, high resolution (size reduction of each scintillator), high counting rate (accelerated event processing) and high sensitivity (high probability of $\gamma$ ray detection).

However, the element Lu-176 is a radioactive substance and three $\gamma$-decays (300 KeV 94%, 202 KeV 78%, 88 KeV 15%) occur concurrently to follow a beta decay ($\beta$-decay) (99.9%, maximum 596 KeV). Due to this, there are cases where a plurality of (two or more) arbitrary radiant rays among these radiant rays is counted coincidentally. This coincidence count cannot be subtracted as "random coincidence count". However, in collection of data in PET, a energy lower limit threshold (300 to 400 KeV) is normally set so as to remove low energy background such as scatter components, as disclosed in, for example, Andrew L. et al.: "On the imaging of very weak sources in an LSO PET Scanner", IEEE MIC 2007, Conf Rec. MO7-5, S Yamamoto et al., "Investigation of single, random, and true counts from natural radioactivity in LSO-based clinical PET", Ann Nucl Med, vol. 19, pp. 109 to 114, 2005. Components other than the $\gamma$-rays (511 KeV) are removed from detection target positrons (that is, radiopharmaceutical). It is reported that self-radioactivity of Lu-176 can be suppressed to almost an ignorable level by setting this energy lower limit threshold to about 400 KeV. In this way, the self-radioactivity of Lu-176 may possibly become background noise, so that it is a main conventional object to suppress the components.

Meanwhile, it is necessary to suppress the self-radioactivity during coincidence counting. A technique or the like for daily checking of detectors (each including a photo multiplier tube (PMT) and an electric circuit) using the self-radioactivity is proposed. The technique is disclosed in, for example, Christof Knoess et al.: "Development of Daily Quality Check Procedure for the High-Resolution Research Tomograph (HRRT) Using Natural LSO Background Radioactivity", IEEE Trans. Nucl. Sci., vol. 49, No. 5, P2074, 2002.

The conventional absorption correction method using the external radiant source and X-ray CT images as stated above is highly accurate and effective. Nevertheless, if the detectors are located to be proximate to the subject with views of improving sensitivity and spatial resolution, a space for mounting a collimated external radiant source, a mechanism that rotates the radiant source (radiant source rotation mechanism) and the like is not often secured. Furthermore, in case of a PET mammography device applied to mammograms for detecting a breast cancer, it is necessary to make a body (breast) of a subject as proximate to the detectors as possible. If an interior of the subject can be considered a uniform absorber, the technique for extracting a profile of the subject from emission data and images, regarding the interior as the uniform absorber and conducting an absorption correction is used. However, if radioactive accumulation is quite small on edges of the subject, the profile cannot be extracted and profile extraction accuracy is deteriorated. Moreover, since distribution is extremely offset on the edges of the subject, the profile extraction accuracy may possibly be deteriorated. In this way, stable profile information cannot be acquired and stable absorption correction cannot be conducted depending on an accumulation situation of the radiopharmaceutical.

SUMMARY OF THE INVENTION

The present invention has been made in view of these circumstances. It is an object of the present invention to provide a nuclear medicine diagnosis device, a form tomography diagnosis device, a nuclear medicine data arithmetic processing method and a form tomogram arithmetic processing method capable of conducting stable absorption correction and capable of being used to process and diagnose nuclear medicine data or to grasp form information.

To attain this object, a nuclear medicine diagnosis device, a form tomography diagnosis device, a nuclear medicine data arithmetic processing method and a form tomogram arithmetic processing method according to the present invention are constituted as follows.

A nuclear medicine diagnosis device according to one aspect of the present invention is a nuclear medicine diagnosis device for obtaining nuclear medicine data on a subject injected with a radiopharmaceutical based on radiant rays generated from the subject, including:

a radiation detection unit configured to contain an element emitting a plurality of radiant rays simultaneously;

a blank data collection unit collecting coincidence count data as blank data, the coincidence count data being coincidentally counted by causing the radiation detection unit configured to contain the element to count some of the radiant rays emitted from the element contained in the radiation detection unit and causing another radiation detection unit to count other radiant rays in a state in which the subject is absent;

a transmission data collection unit collecting coincident count data as transmission data, the coincidence count data being coincidentally counted by causing the radiation detection unit configured to contain the element to count some of the radiant rays emitted from the element contained in the radiation detection unit and another radiation detection unit to count other radiant rays in a state in which the subject is present;

an emission data collection unit collecting coincidence count data as emission data, the coincidence count data being coincidentally counted by causing the radiation detection unit to count the radiant rays generated from the subject injected with the radiopharmaceutical;

an absorption-corrected data calculation unit calculating absorption-corrected data on the subject based on at least one of the blank data collected by the blank data collection unit and the transmission data collected by the transmission data collection unit; and an absorption correction unit absorption-correcting the emission data collected by the emission data collection unit using the absorption-corrected data, and finally obtaining the absorption-corrected emission data as the nuclear medicine data.

The nuclear medicine diagnosis device according to one aspect of the present invention includes the radiation detection unit configured to contain the element emitting a plurality of radiant rays simultaneously. The blank data collection unit collects coincidence count data as blank data, the coincidence count data being coincidentally counted by causing the radiation detection unit configured to contain the element to count some of the radiant rays emitted from the element contained in the radiation detection unit and causing another radiation detection unit to count other radiant rays in a state in which the subject is absent. The transmission data collection unit collects coincident count data as transmission data, the coincidence count data being coincidentally counted by causing the radiation detection unit configured to contain the element to count some of the radiant rays emitted from the element contained in the radiation detection unit and another radiation detection unit to count other radiant rays in a state in which the subject is present. Further, the emission data collection unit collects coincidence count data as emission data, the coincidence count data being coincidentally counted by causing the radiation detection unit to count the radiant rays generated from the subject injected with the radiopharmaceutical. Degrees of absorption (including transmission) of the radiant rays depending on presence and absence of the subject can be recognized based on at least one of the blank data collected by the blank data collection unit and the transmission data collected by the transmission data collection unit. The absorption-corrected data calculation unit can thereby calculate absorption-corrected data on the subject. The absorption correction unit absorption-corrects the emission data collected by the emission data collection unit using the absorption-corrected data, and finally obtains the absorption-corrected emission data as the nuclear medicine data. In this way, although the background data obtained by the self-radioactivity element (element emitting a plurality of radiant rays simultaneously) typified by Lu-176 is originally abandoned, the background data is rather used for the absorption-corrected data. By using the background data for the absorption-corrected data, the radiation detection unit can be made proximate to the subject without need to unnecessarily mount an external radiant source or the like. In addition, stable absorption correction can be conducted without need to unnecessarily use form information obtained from the emission data.

Moreover, if blank data is collected using the radiation detection unit configured to contain the self-radioactivity element (element emitting a plurality of radiant rays simultaneously), a form tomography diagnosis device according to another aspect of the present invention may be constituted as follows.

A form tomography diagnosis device according to another aspect is a form tomography diagnosis device obtaining a form tomogram of a subject injected with a radiopharmaceutical based on radiant rays generated from the subject, including:

a radiation detection unit configured to contain an element emitting a plurality of radiant rays simultaneously;

a blank data collection unit collecting coincidence count data as blank data, the coincidence count data being coincidentally counted by causing the radiation detection unit configured to contain the element to count some of the radiant rays emitted from the element contained in the radiation detection unit and causing another radiation detection unit to count other radiant rays in a state in which the subject is absent;

a transmission data collection unit collecting coincident count data as transmission data, the coincidence count data being coincidentally counted by causing the radiation detection unit configured to contain the element to count some of the radiant rays emitted from the element contained in the radiation detection unit and another radiation detection unit to count other radiant rays in a state in which the subject is present;

a perspective image acquisition unit acquiring a perspective image of the subject based on the blank data collected by the blank data collection unit and the transmission data collected by the transmission data collection unit; and a form tomogram acquisition unit reconstructing the perspective image and acquiring the form tomogram of the subject.

The form tomography diagnosis device according to another aspect of the present invention includes the radiation detection unit configured to contain an element emitting a plurality of radiant rays simultaneously. The blank data collection unit collects coincidence count data as blank data, the coincidence count data being coincidentally counted by causing the radiation detection unit configured to contain the element to count some of the radiant rays emitted from the element contained in the radiation detection unit and causing another radiation detection unit to count other radiant rays in a state in which the subject is absent. The transmission data collection unit collects coincident count data as transmission data, the coincidence count data being coincidentally counted by causing the radiation detection unit configured to contain the element to count some of the radiant rays emitted from the element contained in the radiation detection unit and another radiation detection unit to count other radiant rays in a state in which the subject is present. Degrees of absorption (including transmission) of the radiant rays depending on presence and absence of the subject can be recognized based on the blank data collected by the blank data collection unit and the transmission data collected by the transmission data collection unit. The perspective image acquisition unit can thereby acquire a perspective image of the subject. The form tomogram acquisition unit reconstructs the perspective image and acquires the form tomogram of the subject. In this way, although the background data obtained by the self-radioactivity element (element emitting a plurality of radiant rays simultaneously) typified by Lu-176 is originally abandoned, the background data is rather used for the form tomograms. By rather using the background data, the form tomograms that can be used for a processing and a diagnosis of nuclear medicine data or for grasping form information can be acquired.

Furthermore, a nuclear medicine data arithmetic processing method according to yet another aspect of the present invention is a nuclear medicine data arithmetic processing method of performing an arithmetic processing on nuclear medicine data on a subject injected with a radiopharmaceutical based on radiant rays generated from the subject, comprising thesteps of:

(1) collecting coincidence count data as blank data, the coincidence count data being coincidentally counted by causing a radiation detection unit configured to contain an element emitting a plurality of radiant rays simultaneously to count some of the radiant rays emitted from the element contained in the radiation detection unit and causing another radiation detection unit to count other radiant rays in a state in which the subject is absent;

(2) collecting coincident count data as transmission data, the coincidence count data being coincidentally counted by causing the radiation detection unit configured to contain the element to count some of the radiant rays emitted from the element contained in the radiation detection unit and another radiation detection unit to count other radiant rays in a state in which the subject is present;

(3) collecting coincidence count data as emission data, the coincidence count data being coincidentally counted causing the radiation detection unit to count the radiant rays generated from the subject injected with the radiopharmaceutical;

(4) calculating absorption-corrected data on the subject based on at least one of the blank data and the transmission data;

(5) absorption-correcting the emission data using the absorption-corrected data; and performing the arithmetic processing including the steps (1) to (5) for finally obtaining the absorption-corrected emission data as the nuclear medicine data.

In the nuclear medicine data arithmetic processing method according to yet another aspect of the present invention, in the step (1), coincidence count data is collected as blank data, the coincidence count data being coincidentally counted by causing a radiation detection unit configured to contain an element emitting a plurality of radiant rays simultaneously to count some of the radiant rays emitted from the element contained in the radiation detection unit and causing another radiation detection unit to count other radiant rays in a state in which the subject is absent. In the step (2), coincident count data is collected as transmission data, the coincidence count data being coincidentally counted by causing the radiation detection unit configured to contain the element to count some of the radiant rays emitted from the element contained in the radiation detection unit and another radiation detection unit to count other radiant rays in a state in which the subject is present. In the step (3), coincidence count data is collected as emission data, the coincidence count data being coincidentally counted by causing the radiation detection unit to count the radiant rays generated from the subject injected with the radiopharmaceutical. Degrees of absorption (including transmission) of the radiant rays depending on presence and absence of the subject can be recognized based on at least one of the blank data collected by the blank data collection unit and the transmission data collected by the transmission data collection unit. In the step (4), absorption-corrected data on the subject can be thereby calculated. In the step (5), the emission data is absorption-corrected using the absorption-corrected data, and the absorption-corrected emission data is finally obtained as the nuclear medicine data. The arithmetic processing including these steps (1) to (5) is performed on the nuclear medicine data. In this way, by rather using the background data obtained by the element emitting a plurality of radiant rays simultaneously for the absorption-corrected data, stable absorption correction can be conducted.

Moreover, if blank data is collected using the radiation detection unit configured to contain the self-radioactivity element (element emitting a plurality of radiant rays simultaneously), a form tomogram arithmetic processing method according to still another aspect of the present invention may be constituted as follows.

A form tomogram arithmetic processing method according to still another aspect of the present invention is a form tomogram arithmetic processing method of performing an arithmetic processing on a form tomogram of a subject injected with a radiopharmaceutical based on radiant rays generated from the subject, including the steps of:

(1) collecting coincidence count data as blank data, the coincidence count data being coincidentally counted by causing a radiation detection unit configured to contain an element emitting a plurality of radiant rays simultaneously to count some of the radiant rays emitted from the element contained in the radiation detection unit and causing another radiation detection unit to count other radiant rays in a state in which the subject is absent;

(2) collecting coincident count data as transmission data, the coincidence count data being coincidentally counted by causing the radiation detection unit configured to contain the element to count some of the radiant rays emitted from the element contained in the radiation detection unit and another radiation detection unit to count other radiant rays in a state in which the subject is present;

(6) acquiring a perspective image of the subject based on the blank data and the transmission data; and performing the arithmetic processing including the steps (1), (2), and (6) for reconstructing the perspective image and obtaining the form tomogram of the subject.

In the form tomogram arithmetic processing method according to still another aspect of the present invention, in the step (1), coincidence count data is collected as blank data, the coincidence count data being coincidentally counted by causing a radiation detection unit configured to contain an element emitting a plurality of radiant rays to count some of the radiant rays emitted from the element contained in the radiation detection unit and causing another radiation detection unit to count other radiant rays in a state in which the subject is absent. In the step (2), coincident count data is collected as transmission data, the coincidence count data being coincidentally counted by causing the radiation detection unit configured to contain the element to count some of the radiant rays emitted from the element contained in the radiation detection unit and another radiation detection unit to count other radiant rays in a state in which the subject is present. Degrees of absorption (including transmission) of the radiant rays depending on presence and absence of the subject can be recognized based on the blank data and the transmission data. In the step (6), a perspective image of the subject can be thereby acquired. The perspective image is reconstructed to obtain the form tomogram of the subject. The arithmetic processing including these steps (1), (2), and (6) is performed. In this way, by rather using the background data obtained by the element emitting a plurality of radiant rays simultaneously, the form tomograms that can be used for a processing and a diagnosis of nuclear medicine data or for grasping form information can be acquired.

In the above-stated aspects of the present invention, specific examples of obtaining the absorption-corrected data based on one of the blank data and transmission data include calculating the absorption-corrected data by extracting a profile of the subject only using the transmission data and creating an absorption coefficient map of the subject, and calculating the absorption-corrected data by extracting a profile of the subject using the transmission data and the blank data and creating an absorption coefficient map of the subject. Needless to say, another specific example, the absorption-corrected data can be calculated by calculating an inverse of a transmission factor of the subject obtained based on a ratio of the transmission data to the blank data without creating the absorption coefficient map.

Furthermore, as an example of calculating the absorption-corrected data by extracting a profile of the subject using the transmission data and the blank data and creating an absorption coefficient map of the subject, the profile of the subject is extracted based on a ratio of the transmission data to the blank data or a difference between the transmission data and the blank data.

As an example of calculating the absorption-corrected data by extracting a profile of the subject only using the transmission data and creating an absorption coefficient map of the subject, the absorption coefficient map may be a map on assumption that an interior of the subject is regarded as an absorber or the absorption coefficient map may be a map on assumption that an interior of the subject is regarded as an absorber constituted by a plurality of absorption coefficient segments. In case of the latter map, the profile of the subject and internal form information that form basis for the absorption coefficient segments are extracted only using the transmission data.

Likewise, as an example of calculating the absorption-corrected data by extracting a profile of the subject using the transmission data and the blank data and creating an absorption coefficient map of the subject, the absorption coefficient map may be a map on assumption that an interior of the subject is regarded as an absorber or the absorption coefficient map may be a map on assumption that an interior of the subject is regarded as an absorber constituted by a plurality of absorption coefficient segments. In case of the latter map, the profile of the subject and internal form information that form basis for the absorption coefficient segments are extracted only using the transmission data and the blank data.

As can be seen, in case of the latter map, a more accurate absorption coefficient map can be created according to an actual subject and more accurate absorption correction can be thereby conducted.

Moreover, the absorption coefficient map is not necessarily used solely. The absorption coefficient map may be combined with a conventional profile extraction technique so as to improve profile extraction accuracy. For example, the profile of the subject may be extracted using emission data as well as the transmission data and the blank data.

The step (2) of collecting the transmission data and the step (3) of collecting the emission data may be executed either separately or simultaneously.

In the former case, the coincidence count data coincidentally counted in the step (2) differs from the coincidence count data coincidentally counted in the step (3). In the latter case, the coincidence count data coincidentally counted in the step (2) and the coincidence count data coincidentally counted in the step (3) are data acquired by one shooting, and the data acquired by one shooting may be separated into coincidence count data for collection of the transmission data and coincidence count data for collection of the emission data so as to collect the transmission data in the step (2) and to collect the emission data in the step (3).

Specific examples of a separation method are as follows. The data acquired by one shooting may be separated based on an energy from the radiant rays during counting of the radiant rays. The data acquired by one shooting may be separated based on time difference information during counting of the radiant rays. The data acquired by one shooting may be separated based on spatial information obtained by each of the radiation detection unit configured to contain the element and a radiation detection unit configured not to contain the element if the radiation detection unit configured to contain the element is combined with the radiation detection unit configured not to contain the element.

A specific method of separating the data acquired by one shooting based on the spatial information is as follows. By coincidentally counting the radiant rays while driving a ring radiation detection mechanism configured to arrange the radiation detection unit configured to contain the element and the radiation detection unit configured not to contain the element into a ring shape to surround a body axis of the subject to rotate around the body axis of the subject, the spatial information in which the transmission data based on the radiant rays emitted from the radiation detection unit configured to contain the element on LORs connecting paired radiation detection units used for coincidence counting and the emission data based on the radiant rays generated from the subject injected with the radiopharmaceutical on one of the LORs related to the radiation detection unit configured to contain the element are mixed up is collected, the LORs being abbreviation of lines of response. The spatial information only on the emission data is collected based on the radiant rays generated from the subject injected with the radiopharmaceutical on one of the LORs related only to the radiation detection unit configured not to contain the element among the LORs. The spatial information only on the collected emission data is subtracted from the spatial information in which the collected emission data and the collected transmission data are mixed up, thereby separating the data acquired by one shooting for coincidence counting of the radiant rays while causing the rotary drive mechanism to drive the ring radiation detection mechanism to rotate about the body axis of the subject.

In the nuclear medicine diagnosis device, the form tomography diagnosis device, the nuclear medicine data arithmetic processing method and the form tomogram arithmetic processing method according to the present invention, by rather using background data obtained by the element emitting a plurality of radiant rays simultaneously for absorption-corrected data, stable absorption correction can be conducted. Furthermore, by rather using the background data, form tomograms that can be used for a processing and a diagnosis of nuclear medicine data or for grasping form information can be acquired.

BRIEF DESCRIPTION OF THE DRAWINGS

For the purpose of illustrating the invention, there are shown in the drawings several forms which are presently preferred, it being understood, however, that the invention is not limited to the precise arrangement and instrumentalities shown.

FIG. 3 is a schematic side view showing a specific configuration of a radiation detector in each detector plate;

FIGS. 4A and 4B are schematic diagrams showing modes of scintillators constituting each radiation detector, respectively;

FIG. 9 is a flowchart showing a flow of a nuclear medicine diagnosis including an arithmetic processing method according to the second embodiment;

FIG. 15 is a flowchart showing a flow of a form tomography diagnosis including an arithmetic processing method according to the third embodiment.

DESCRIPTION OF THE PREFERRED EMBODIMENTS

Preferred embodiments of the present invention will be described in detail below reference to the accompanying drawings.

First Embodiment

Figure 1:
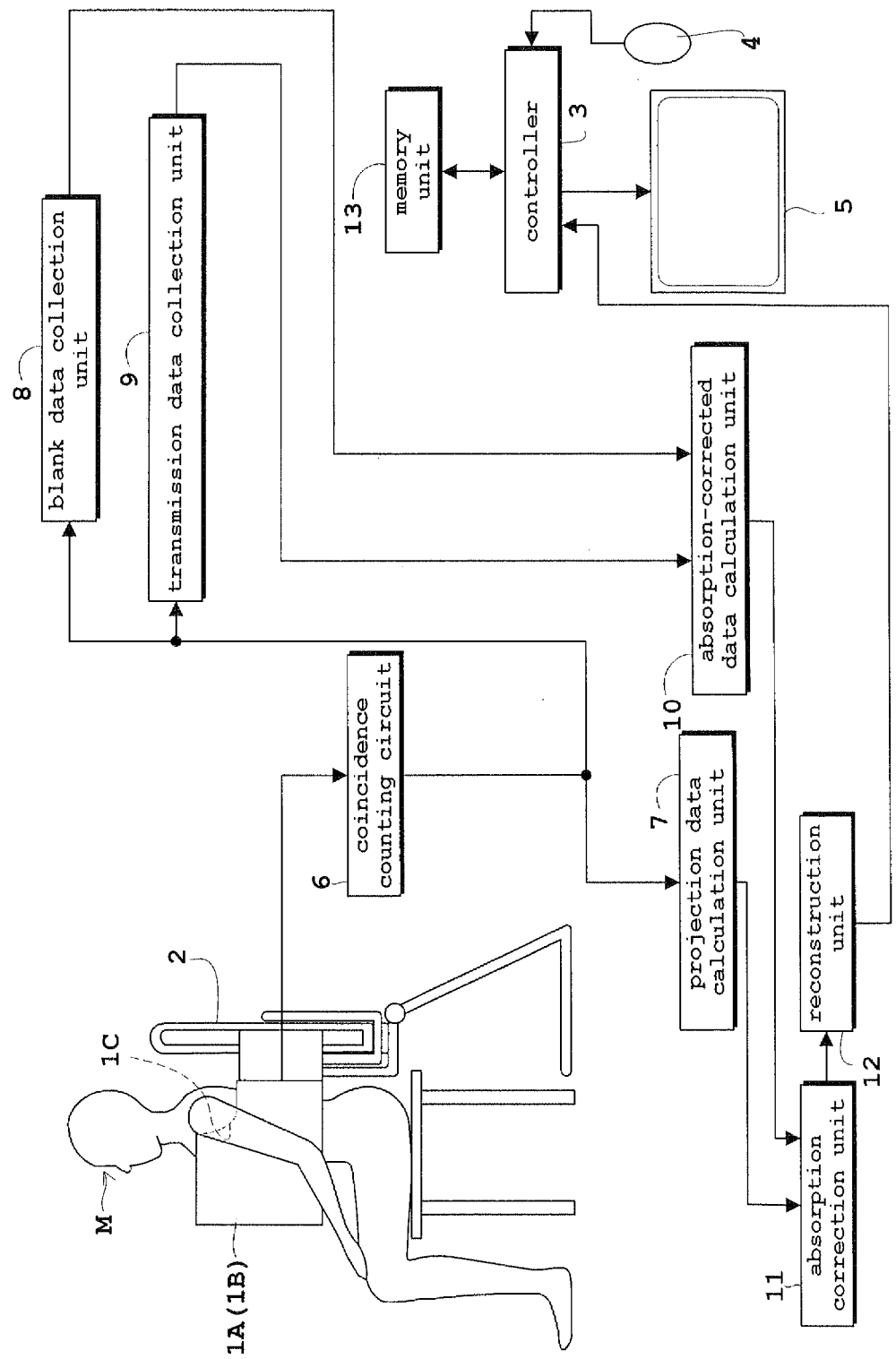
FIG. 1 is a side view and a block diagram of a positron emission tomography (PET) mammography device according to a first embodiment of the present invention.
Figure 2A:
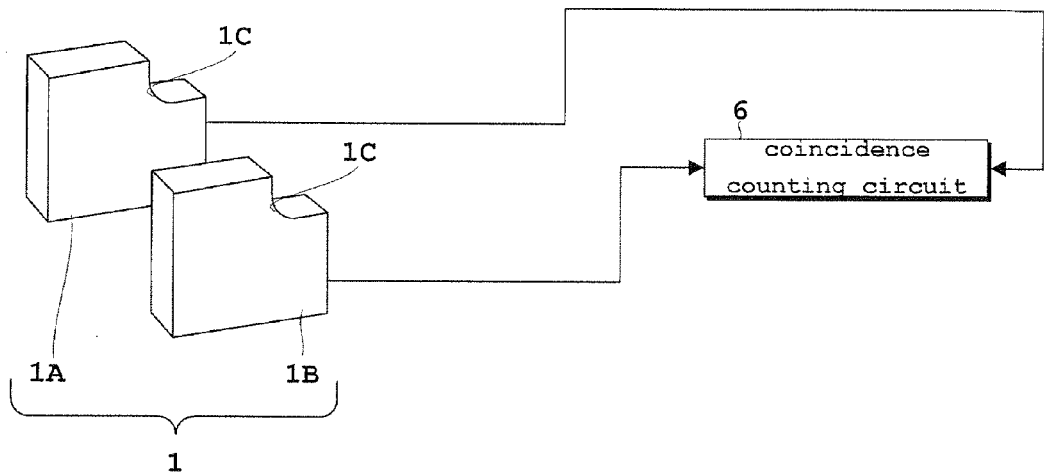
FIG. 2A is a block diagram showing surroundings of detector plates employed in the PET mammography device according to the first embodiment and FIG. 2B is a schematic diagram of each of the detector plates.
Figure 2B:
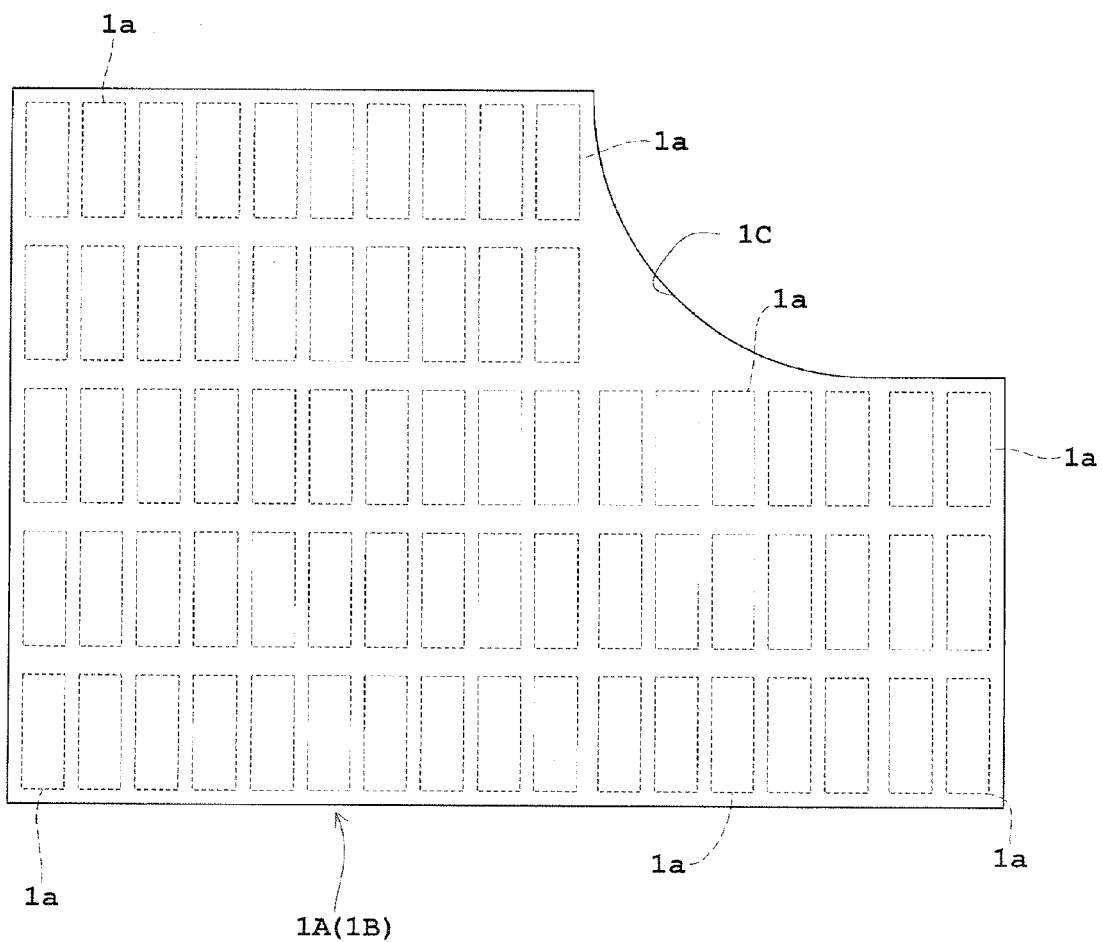

FIG. 1 is a side view and a block diagram of a positron emission tomography (PET) mammography device according to a first embodiment. FIGS. 2A and 2B are a block diagram showing surroundings of detector plates used in the PET mammography device according to the first embodiment and a schematic diagram of each of the detector plates, respectively. FIG. 3 is schematic side view showing a specific configuration of a radiation detector in each detector plate. FIGS. 4A and 4B are schematic diagrams showing modes of scintillators constituting each radiation detector, respectively. In the first embodiment as well as second and third embodiments to be described later, a PET device will be described by way of example as a nuclear medicine diagnosis device. In the first embodiment, the PET mammography device applied to mammograms for breast cancer detection will be described as an example of the PET device.

As shown in the block diagrams of FIGS. 1 and 2A, the PET mammography device according to the first embodiment includes a detector unit 1, a support mechanism 2, a controller 3, an input unit 4, an output unit 5, a coincidence counting circuit 6, a projection data calculation unit 7, a blank data collection unit 8, a transmission data collection unit 9, an absorption-corrected data calculation unit 10, an absorption correction unit 11, a reconstruction unit 12 and a memory unit 13. The detector unit 1 is configured to include two detector plates 1A and 1B opposed to each other across a subject M. As shown in the schematic diagram of FIG. 2B, each of the detector plates 1A and 1B is configured so that a plurality of radiation detectors 1a is arranged in parallel according to a notch 1C. Each radiation detector 1a corresponds to radiation detection unit according to the present invention.

As shown in FIG. 3, the radiation detector 1a is configured to include a scintillator block 21 constituted by a combination of a plurality of scintillators serving as detection components, a light guide 22 optically coupled to the scintillator block 3a and a photo multiplier tube (PMT) 23 optically coupled to the light guide 22. Each scintillator in the scintillator block 21 emits light by an incident γ ray, converts the γ ray into light, and thereby detects the γ ray. It is to be noted that the radiation detector 1a detects not only γ rays but also β rays.

In the first embodiment as well as the second and third embodiments to be described later, each scintillator is configured to contain an element simultaneously emitting a plurality of radiant rays (including β rays and the like as well as γ rays). In the specification, "configured to contain an element . . . " means as follows. As shown in FIG. 4A, for example, entire scintillators 21A (see a hatched part indicated by positive slopes in FIG. 4A) consist of a substance having self-radioactivity (element emitting a plurality of radiant rays simultaneously) typified by Lu-176 or a self-radioactivityadded substance (such as Lu-containing GSO). Alternatively, as shown in FIG. 4B, a scintillator 21B consists of a substance that does not have self-radioactivity typified by, for example, GSO. A scintillator 21C (see a hatched part indicated by positive slopes in FIG. 4B) is constituted by bonding a thin-film tape consisting of a substance having self-radioactivity or a self-radioactivity-added substance to the scintillator 21B. Alternatively, a scintillator 21C is constituted by coating a coating agent made of a substance having self-radioactivity or a self-radioactivity-added substance onto the scintillator 21B (see a hatched part indicated by positive slopes in FIG. 4B).

If the scintillators configured to contain such a self-radioactivity element (element emitting a plurality of radiant rays simultaneously) constitute each radiation detector 1a (see FIGS. 2B and 3), three γ-decays (300 KeV 94%, 202 KeV 78%, 88 KeV 15%) occur concurrently to follow a β-decay (99.9%, maximum 596 KeV). As a result, a plurality of (two or more) arbitrary radiant rays among these radiant rays is emitted from the scintillators. Some of the radiant rays are detected and counted by the radiation detectors 1a (emitting the radiant rays) whereas the other radiant rays are detected and counted by the other radiation detectors 1a (that is, the radiation detectors 1a that do not emit the radiant rays). If the emitted radiant rays are β rays, the scintillators that emitted the rays, the scintillators nearby or the radiation detectors 1a nearby detect the β rays. If the emitted radiant rays are γ rays, one radiation detector 1a including the scintillators that emits the rays or the other radiation detectors 1a (including the radiation detectors nearby) detect and count the rays.

The γ ray will now be described. As already described, the scintillator blocks 21 emit γ rays and convert each γ ray into light. The light guide 22 guides the light converted by the scintillator blocks 21 to the PMT 23. The PMT 23 photoelectrically converts the light guided by the light guide 22 into an electric signal and outputs the electric signal to the coincidence counting circuit 6 as shown in FIGS. 1 and 2A.

Referring back to FIG. 1, the support mechanism 2 supports the detector plates 1A and 1B opposed to each other with the body (such as breast) of the subject M held therebetween, whereby the detector plates 1A and 1B are configured to be opposed to each other. The controller 3 exercises an integrated control over the respective constituent elements of the PET mammography device according to the first embodiment. The controller 3 is configured to include a central processing unit (CPU) and the like.

The input unit 4 transmits data or a command input by an operator to the controller 3. The input unit 4 is configured to include a pointing device typified by a mouse, a keyboard, a joystick, a track ball and/or a touch panel. The output unit 5 is configured to include a display unit typified by a monitor, a printer and the like.

The memory unit 13 is configured to include a storage medium typified by a ROM (Read-only Memory) or a RAM (Random-Access Memory). In the first embodiment, projection data calculated by the projection data calculation unit 7, tomograms reconstructed by the reconstruction unit 12, blank data collected by the blank data collection unit 8, transmission data collected by the transmission data collection unit 9, absorption-corrected data calculated by the absorption collection unit 7, projection data absorption-corrected by the absorption correction unit 11 and the like are written to the RAM and read from the RAM if it is necessary to do so. Programs or the like for conducting various nuclear medicine diagnoses are stored in the ROM in advance. The controller 3 executes the programs, thereby conducting nuclear medicine diagnoses conducted according to the programs, respectively.

The projection data calculation unit 7, the blank data collection unit 8, the transmission data collection unit 9, the absorption-corrected data calculation unit 10, the absorption collection unit 11, and the reconstruction unit 12 are realized by, for example, causing the controller 3 to execute programs stored in the memory unit 13 serving as the storage medium typified by the ROM and the like or commands input by the input unit 4 typified by the pointing device or the like.

The scintillator blocks 21 (see FIG. 2A) convert each of γ rays emitted from the subject M injected with a radiopharmaceutical, that is, a radioactive isotope (RI) into light. The PMT 23 (see FIG. 2A) photoelectrically converts the light into an electric signal and outputs the electric signal to the coincidence counting circuit 6 as image information (pixels).

Specifically, if the radiopharmaceutical is administered into the subject M, positrons of positron-emitting RI are annihilated and a pair of γ rays is thereby generated. The coincidence counting circuit 6 checks positions of the scintillator blocks 21 (see FIG. 2A) and a γ-ray incident timing and determines that the transmitted image information is appropriate data only when γ rays are simultaneously incident on the two scintillator blocks 21 opposed to each other across the subject M. If γ rays are incident only on one of the scintillator blocks 21, the coincidence counting circuit 6 deals with the γ rays not as γ rays generated as a result of annihilation of positrons but as noise. Further, the coincidence counting circuit 6 determines the image information transmitted to the circuit 6 as noise and abandons the image information.

In case of the radiation detector 1a including the scintillator block 21 configured to contain the self-radioactivity element, not only γ rays from the radiopharmaceutical but also γ rays emitted from the scintillator block 21 configured to contain the self-radioactivity element are incident on the scintillator block 21 of the radiation detector 1a. Even if such γ rays are simultaneously incident on the two scintillator blocks 21 opposed to each other across the subject M, the coincidence counting circuit 6 deals with them as "coincidence count data". The data obtained by the self-radioactivity (that is, data counted by the coincidence counting circuit 6 by incidence of γ rays emitted from the scintillator blocks 21 each configured to contain the self-radioactivity element) is background data. The background data is used in the first embodiment as well as the second and third embodiments to be described later.

The coincidence counting circuit 6 transmits image information on the components from the radiopharmaceutical among the image information on the detected γ rays to the projection data calculation unit 7. The coincidence counting circuit 6 transmits image information on self-radioactivity components among the image information on the detected γ rays to the transmission data collection unit 9. Further, the coincidence counting circuit 6 transmits image information obtained by the self-radioactivity in a state in which the subject M is not present among the image information on the detected γ rays to the blank data collection unit 8. The projection data calculation unit 7 calculates the image information transmitted from the coincidence counting circuit 6 as projection data and transmits the projection data to the absorption correction unit 11. The projection data calculated by the projection data calculation unit 7 is also referred to as "emission data". The projection data calculation unit 7 corresponds to an emission data collection unit according to the present invention.

The blank data collection unit 8 collects the data obtained by the self-radioactivity in a state in which the subject M is not present as blank data. The transmission data collection unit 9 collects the data obtained by the self-radioactivity in a state in which the subject M is present as transmission data. The blank data collected by the blank data collection unit 8 and the transmission data collected by the transmission data calculation unit 9 are transmitted to the absorption-corrected data calculation unit 10. The blank data collection unit 8 corresponds to a blank data collection unit according to the present invention and the transmission data collection unit 9 corresponds to a transmission data collection unit according to the present invention.

The absorption-corrected data calculation unit 10 calculates absorption-corrected data on the subject M based on the blank data collected by the blank data collection unit 8 and the transmission data collected by the transmission data collection unit 9. In the first embodiment as well as the second embodiment to be described later, the absorption collection data calculation unit 10 calculates absorption collection data by extracting a profile of the subject M from a ratio to the transmission data to the blank data and creating an absorption correction map of the subject M. The absorption collection data calculation unit 10 transmits the calculated absorption-corrected data to the absorption correction unit 11. The absorption correction unit 11 absorption-corrects the projection data calculated by the projection data calculation unit 7 in light of absorption of γ rays within the subject M by reflecting the absorption-corrected data calculated by the absorption-corrected data calculation unit 10 in the projection data calculated by the projection data calculation unit 7. The absorption correction unit 11 transmits the absorption-corrected projection data to the reconstruction unit 12. The absorption-corrected data calculation unit 10 corresponds to an absorption-corrected data calculation unit according to the present invention. The absorption correction unit 11 corresponds to an absorption correction unit according to the present invention.

The absorption correction unit 11 transmits the absorption-corrected projection data to the reconstruction unit 12. The reconstruction unit 12 reconstructs the projection data and obtains tomograms in light of the absorption of γ rays within the subject M. In this way, by providing the absorption correction unit 11 and the reconstruction unit 12 in the PET mammography device according to the first embodiment, the PET mammography device corrects the projection data based on the absorption-corrected data and corrects the tomograms. The reconstruction unit 12 transmits the corrected tomograms to the output unit 5, the memory unit 13 and the like via the controller 3.

Figure 5:
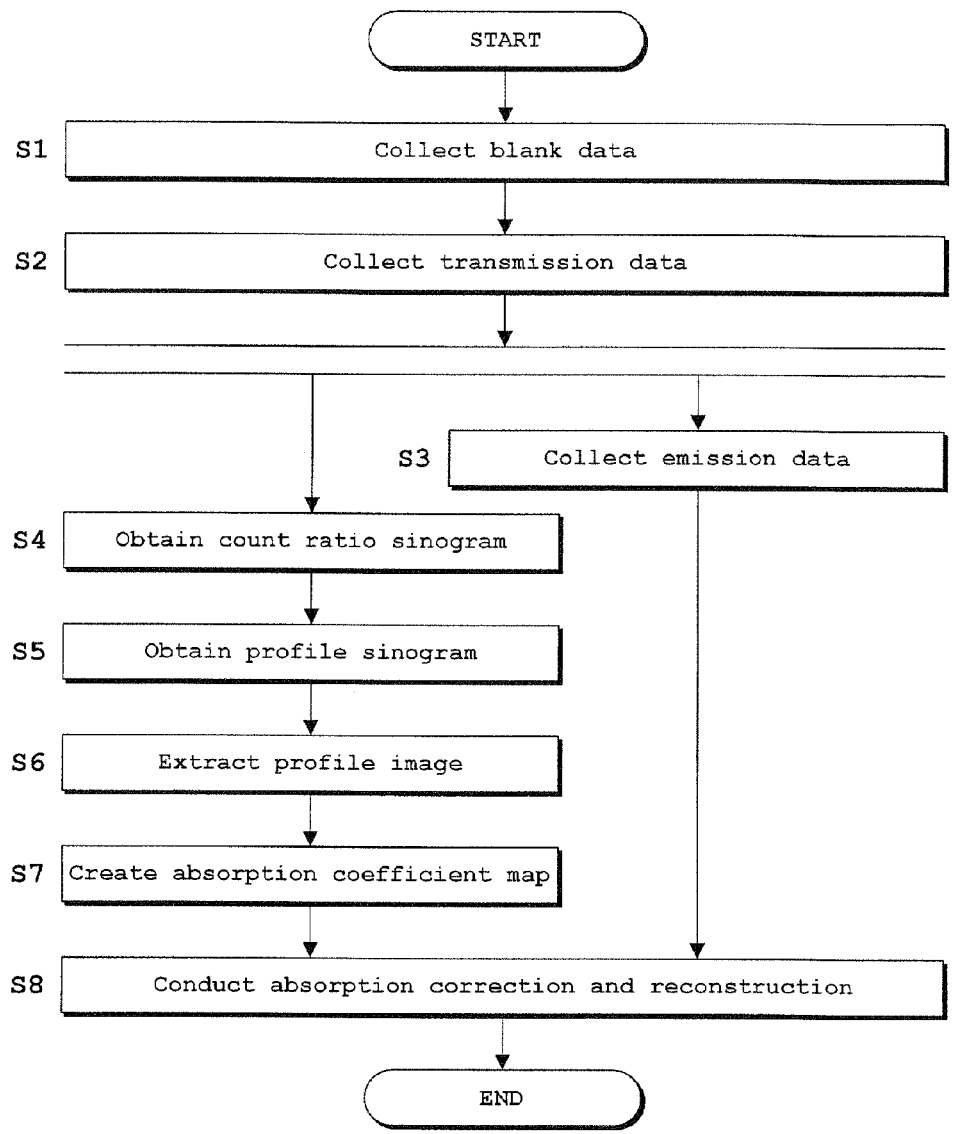
FIG. 5 is a flowchart showing a flow of a nuclear medicine diagnosis including an arithmetic processing method according to the first embodiment.
Figure 6:
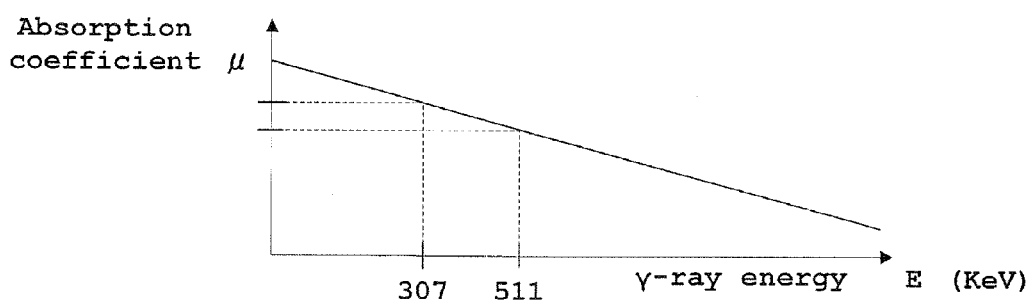
FIG. 6 is a graph typically showing an absorption coefficient relative to γ-ray energy.

A method of performing an arithmetic processing on each data (an arithmetic processing method) will next be described with reference to FIGS. 5 and 6. FIG. 5 is a flowchart showing a flow of a nuclear medicine diagnosis including the arithmetic processing method according to the first embodiment. FIG. 6 is a graph typically showing an absorption coefficient relative to γ-ray energy. The arithmetic processing method according to the first embodiment will be described while γ rays from the radionuclide administered into the subject M are discriminated from γ rays emitted from the scintillators by adopting a "discrimination technique based on photonic energy" to be described later by way of example.

(Step S1) Collect Blank Data

In a state in which the subject M is not present and in which a plurality of radiation detectors 1a each including the scintillator block 21 configured to contain the self-radioactivity element are arranged, the energy lower limit is set to, for example, 200 KeV. Self-radioactivity γ rays (307 KeV, 202 KeV and 88 KeV) emitted from the scintillator blocks 21 can be thereby efficiently collected. The γ rays emitted from the scintillator blocks 21 each configured to contain the self-radioactivity element for predetermined time (such as ten hours) are counted. At this time, some radiation detectors 1a each including the scintillator block 21 configured to contain the self-radioactivity element (that is, scintillators emitting γ rays) count some γ rays among the emitted γ rays. The other radiation detectors 1a count the other γ rays. By doing so, the blank data collection unit 8 collects the coincidence count data coincidentally counted by the coincidence counting circuit 6 not as γ rays from the radiopharmaceutical but as background data obtained by the self-radioactivity in the state in which the subject M is not present and as blank data. Step S1 corresponds to a step (1) according to the present invention.

(Step S2) Collect Transmission Data

Next, in a state in which the subject M is present and in which a plurality of radiation detectors 1a each including the scintillator block 21 configured to contain the self-radioactivity element is arranged, γ rays emitted from the scintillator blocks 21 each configured to contain the self-radioactivity element for predetermined time are counted. At this time, in the first embodiment, the energy lower limit is set to, for example, 200 KeV, the self-radioactivity γ rays (307 KeV, 202 KeV and 88 KeV) emitted form the scintillator blocks 21 can be thereby efficiently collected. Each radiation detector 1a including the scintillator block 21 configured to contain the self-radioactivity element (that is, scintillators emitting γ rays) counts some γ rays among the emitted γ rays or β rays. The radiation detectors 1a other than the radiation detector 1a count the other γ rays transmitted by the subject M and reaching the other radiation detectors 1a. By so counting, the transmission data collection unit 9 collects the coincidence count data coincidentally counted by the coincidence counting circuit 6 as background data obtained by the self-radioactivity in the state in which the subject M is present and as transmission data. Step S2 corresponds to a step (2) according to the present invention. Preferably, no radioactive substance is administered into the subject M. However, even if the radioactive substance is administered into the subject M, it is possible to obtain data having a high contribution rate to background components by the self-radioactivity by optimizing an energy width.

(Step S3) Collect Emission Data

Emission data is collected by simultaneously counting γ rays emitted from the subject M. Since the energy of a γ ray is 511 KeV, the γ rays are collected at an energy width covering this energy range. The emission data is collected simultaneously or independently of and in parallel to collection of the transmission data, that is, step S2. An order of steps S2 and S3 may be arbitrarily set. Therefore, step S3 may be executed after step S2, step S3 may be executed before step S2 or step S3 may be executed simultaneously with or independently of and in parallel to step S2.

Similarly to step S2, in the state in which the subject M is present, the radiopharmaceutical is administered into the subject M, and in which a plurality of radiation detectors 1a each including the scintillator block 21 configured to contain the self-radioactivity element, γ rays are counted. By setting the energy lower limit threshold to 400 KeV, γ rays from the self-radioactivity element (background data) can be suppressed to almost an ignorable level. By so counting, the projection data calculation unit 7 calculates the coincidence count data coincidentally counted by the coincidence counting circuit 6 as γ rays from the radiopharmaceutical and as emission data. Step S3 corresponds to a step (3) according to the present invention.

(Step S4) Obtain Count Ratio Sinogram

The absorption-corrected data calculation unit 10 calculates absorption-corrected data by developing a ratio of the blank data (B) collected by the blank data collection unit 8 in step S1 to the transmission data (T) collected by the transmission data collection unit 9 in step S2 to a sinogram. Specifically, the absorption-corrected data calculation unit 10 divides the blank data (B) by the transmission data (T) for each of pixels on the sinogram.

(Step S5) Obtain Profile Sinogram

The sinogram resulting from development and division of the sinogram described above can ensure stable profile information even on edges of the subject M without dependence on an accumulation situation of the radiopharmaceutical ("profile sinogram").

(Step S6) Extract Profile Image

The absorption correction calculation unit 10 develops the profile sinogram obtained in step S5to projection data other than the sinogram (equal in dimensions to the projection data calculated by the projection data calculation unit 7), thereby extracting profile images of the subject M.

(Step S7) Create Absorption Coefficient Map

A value obtained by dividing the blank data (B) by the transmission data (T) is a transmission factor of the subject M. Therefore, the absorption-corrected data calculation unit 10 creates an absorption coefficient map by calculating a logarithm of the value and reconstructing images. In step S7, the absorption-corrected data calculation unit 10 creates the absorption coefficient map while regarding the interior of the subject M as a uniform absorber.

In step S7, the blank data and the transmission data based on which the absorption coefficient map is created are derived from γ rays of the energy of 307 KeV and the like. Due to this, the absorption coefficient map is also related to the γ rays of 307 KeV. The absorption-corrected data calculation unit 10 may extract the profile from the absorption coefficient map at 307 KeV, allocate a theoretical absorption coefficient for γ rays of 511 KeV and conduct absorption correction in step S8 to be described later. Alternatively, the absorption-corrected data calculation unit 10 may convert the absorption coefficient map for 307 KeV into an absorption coefficient map for 511 KeV since the emission data to be absorption-corrected is the coincidence count data at 511 KeV. For example, as shown in FIG. 6, the absorption-corrected data calculation unit 10 may create a graph of an absorption coefficient μ (such as an absorption coefficient of water) relative to γ-ray energy E or a lookup table showing a correspondence between the γ-ray energy and the absorption coefficient in advance, convert the absorption coefficient at 307 KeV into that at 511 KeV while referring to the graph or lookup table, create the absorption coefficient map for 511 KeV and conduct absorption correction using this absorption coefficient map for 511 KeV in step 8 to be described later. Steps S4 to S7 correspond to a step (4) according to the present invention.

Moreover, the steps of calculating the absorption-corrected data, that is, steps S4 to S7 are executed simultaneously with or independently of and in parallel to the step of collecting the emission data, that is, step S3. An order of steps S3 and S4 to S7 may be arbitrarily set. Therefore, steps S4 to S7 may be executed after step S3, Steps S4 to S7 may be executed before step S3 or steps S4 to S7 may be executed simultaneously with or independently of and in parallel to step S3.

In summary, if step S3 (the step (3) according to the present invention) is executed after step S2 (the step (2)), steps S4 to S7 (the step (4)) are executed (A) after step S3 (the step (3)), (B) after step S2 (step (2)) and before step S3 (step (3)) or (C) simultaneously or independently of and in parallel to step S3 (step (3)). Alternatively, if step S3 (step (3)) is executed before step S2 (step (2)) or simultaneously or independently of and in parallel to step S2 (step (2)), steps S4 to S7 (step (4)) are executed after step S2 (step (2)).

(Step S8) Conduct Absorption Correction and Reconstruction

Using the absorption-corrected data (absorption coefficient map in the first embodiment) calculated by the absorption-corrected data calculation unit 10 in steps S4 to S7, the emission data calculated by the projection data calculation unit 7 in step S3 is absorption-corrected. The reconstruction unit 12 reconstructs the absorption-corrected projection data (that is, emission data) and finally obtains tomograms as nuclear medicine data. During the absorption correction, normally used processing such as a normalization processing, a scatter compensation processing and the like other than the absorption correction processing may be performed. Step S8 corresponds to a step (5) according to the present invention.

The PET mammography device according to the first embodiment configured as stated above includes the radiation detectors 1*a* each configured to contain an element (a self-radioactivity element such as Lu-176) emitting a plurality of radiant rays simultaneously. In the state in which the subject M is not present, the radiation detectors 1*a* each containing the element count some of the γ rays emitted by the element and the other radiation detectors 1*a* count the other γ rays. By doing so, the blank data collection unit 8 collects the coincidentally counted coincidence count data as the blank data in step S1. On the other hand, in the state in which the subject M is present, the radiation detectors 1*a* each containing the element count the γ rays emitted by the element and the other radiation detectors 1*a* count the other γ rays. By doing so, the transmission data collection unit 9 collects the coincidentally counted coincidence count data as the transmission data in step S2. Furthermore, the radiation detectors 1*a* count γ rays emitted from the subject M injected with the radiopharmaceutical. The projection data calculation unit 7 thereby collects the coincidentally counted coincidence count data as the emission data in step S3.

Degrees of absorption (including transmission) of the γ rays depending on presence and absence of the subject M can be recognized based on the blank data collected by the blank data collection unit 8 in step S1 and the transmission data collected by the transmission data collection unit 9 in step S2. Further, the absorption-corrected data calculation unit 10 can calculate the absorption-corrected data (absorption coefficient map in the first embodiment) of the subject M in steps S4 to S7. The absorption correction unit 11 absorption-corrects the emission data collected by the projection data calculation unit 7 using the absorption-corrected data (absorption coefficient map in the first embodiment) to finally obtain the absorption-corrected data (tomograms in the first embodiment) as the nuclear medicine data in step S8. The arithmetic processing from steps S1to S8 are performed on the nuclear medicine data.

As can be seen, the background data obtained by the self-radioactivity (element emitting a plurality of radiant rays simultaneously) typified by Lu-176 is originally abandoned. However, the background data is rather used for the absorption-corrected data. By using the background data for the absorption-corrected data, the radiation detection units typified by the radiation detectors 1*a* can be made proximate to the subject M without need to unnecessarily mount the external radiant source or the like. In addition, stable absorption correction can be conducted without need to unnecessarily use the form information obtained from the emission data.

In the first embodiment, as a specific example of calculating the absorption-corrected data based on the blank data and the transmission data, the profile of the subject M is extracted from the ratio (T/B) of the transmission data (T) to the blank data (B) and the absorption coefficient map of the subject M is created, thereby calculating the absorption-corrected data. In the first embodiment, the absorption coefficient map is a map on the premise that the interior of the subject M is regarded as a uniform absorber.

In the first embodiment, the collection of the transmission data in step S2 and the collection of the emission data in step S3 are executed separately. That is, the collection of the transmission data in the step (2) according to the present invention and the collection of the emission data in the step (3) are executed separately. In the first embodiment, the coincidence count data coincidentally counted in the step (2) differs from the coincidence count data coincidentally counted in the step (3).

Moreover, in the first embodiment, the absorption correction can be conducted without providing the external radiant source. It is, therefore, advantageously possible to make the radiation detectors 1a proximate to the subject M, downsize the device similarly to the PET mammography device and improve device sensitivity. Because of no use of the external radiant source, there is no need to purchase and replace radiant sources, whereby running cost and maintenance cost can be advantageously reduced.

Second Embodiment

A second embodiment of the present invention will be described below with reference to the drawings.

Figure 7:
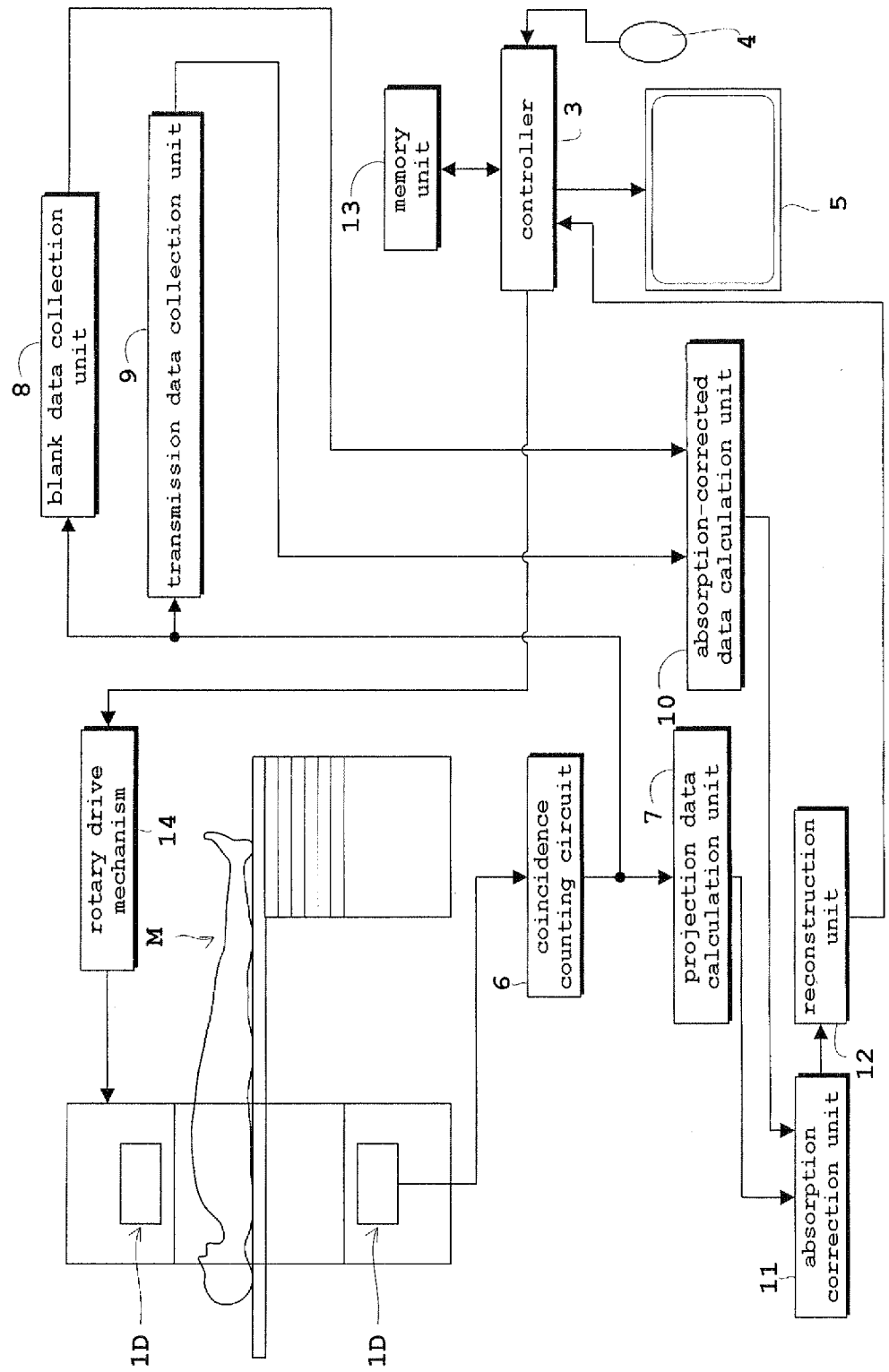
FIG. 7 is a side view and a block diagram of a PET device according to a second embodiment.

FIG. 7 is a side view and a block diagram of a PET device according to the second embodiment. FIG. 8 is a schematic diagram of a ring radiation detection mechanism employed in the PET device according to the second embodiment. In the second embodiment, similarly to the first embodiment, the PET device will be described as a nuclear medicine diagnosis device by way of example. In the second embodiment, the PET device including ring radiation detection mechanisms 1D downsizing of which is realized by making the mechanisms 1D as proximate to the subject M as possible except for the external radiant source will be described by way of example.

As shown in FIG. 7, the PET device according to the second embodiment includes a controller 3, an input unit 4, an output unit 5, a coincidence counting circuit 6, a projection data calculation unit 7, a blank data collection unit 8, a transmission data collection unit 9, an absorption-corrected data calculation unit 10, an absorption correction unit 11, a reconstruction unit 12 and a memory unit 13 similarly to the first embodiment stated above. Since the constituent elements of the PET device are the same as those according to the first embodiment except for the coincidence counting circuit 6, these elements other than the coincidence counting circuit 6 will not be described herein. In the second embodiment, the PET device includes the ring radiation detection mechanisms 1D and a rotary drive mechanism 14 driving the ring radiation detection mechanisms 1D to rotate around a body axis of the subject M in place of the detector unit 1 according to the first embodiment. Each of the ring radiation detection mechanisms 1D corresponds to a ring radiation detection mechanism according to the present invention and the rotary drive mechanism 14 corresponds to a rotary drive mechanism according to the present invention.

Figure 8A:
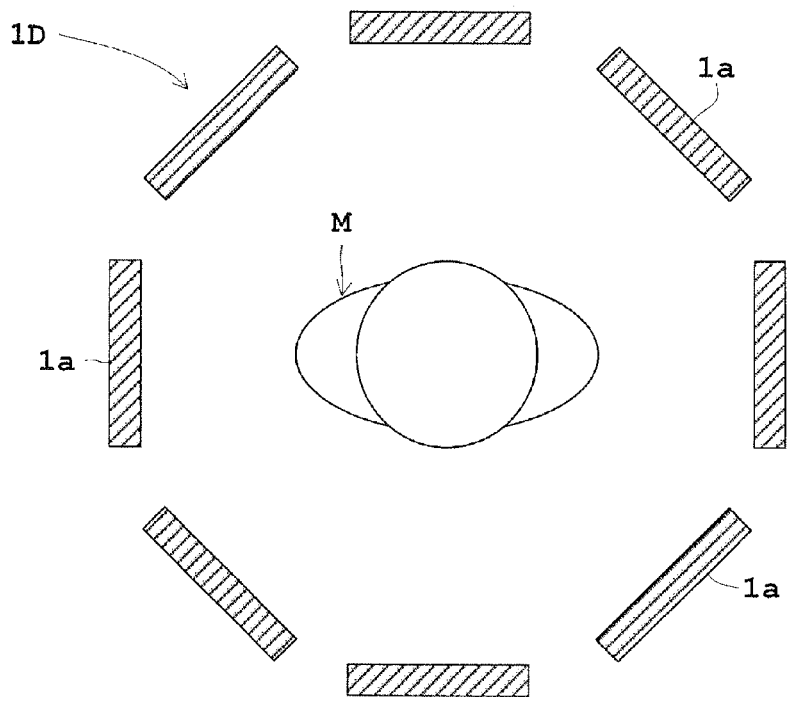
FIGS. 8A and 8B are schematic diagrams of a ring radiation detection mechanism employed in the PET device according to the second embodiment.
Figure 8B:
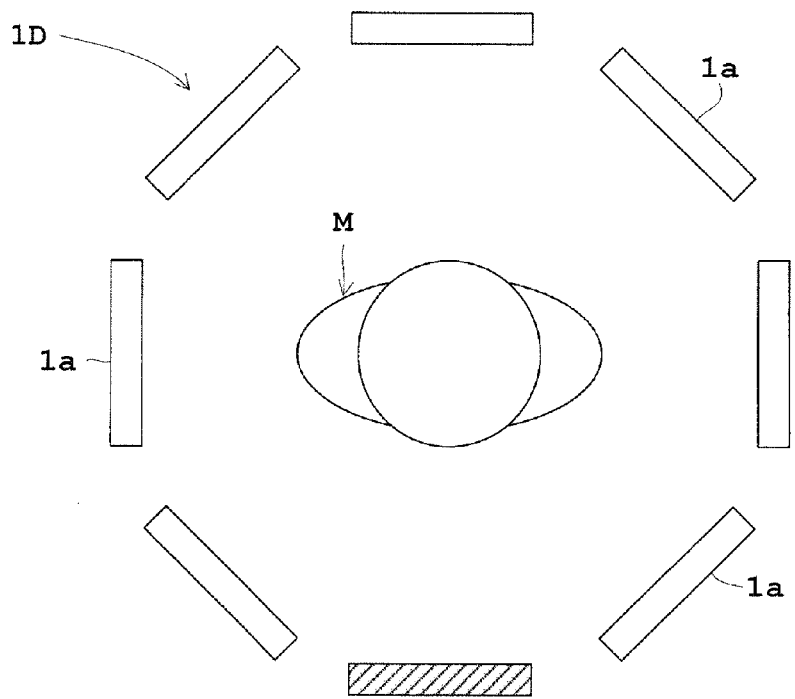

As shown in FIGS. 8A and 8B, each ring radiation detection mechanism 1D is configured to arrange a plurality of radiation detectors 1a into a ring shape to surround the body axis of the subject M. It suffices that the ring radiation detection mechanism 1D includes at least one radiation detectors 1a configured to contain an element emitting a plurality of radiant rays simultaneously (a self-radioactivity element such as Lu-176). For example, as shown in FIG. 8A, the ring radiation detection mechanism 1D may include the radiation detectors 1a each of which is configured to contain a self-radioactivity element (see a hatched part indicated by positive slopes in FIG. 8A). Alternatively, as shown in FIG. 8B, the ring radiation detection mechanism 1D may include a radiation detector 1a configured to contain a self-radioactivity element (see a hatched part indicated by positive slopes in FIG. 8B) only partially and include radiation detectors 1a configured to contain a non self-radioactivity substance typified by GSO. A structure shown in FIG. 8B is effective if data acquired by one shooting is separated based on spatial information to be described later. Since a specific configuration of each radiation detector 1a is similar to that shown in FIG. 3, it will not be described herein. The radiation detector 1a corresponds to a radiation detection unit according to the present invention.

In ordinary nuclear medicine diagnosis, measurement (collection) often starts after an administered medical agent is sufficiently distributed in the body of the subject M by setting some time for distributing the agent into the body of the subject M. It is, therefore, preferable to collect transmission data for absorption correction after administering the agent into the subject M in a distribution stabilized state. Accordingly, it is more preferable to simultaneously execute collection of the transmission data and ordinary collection of emission data for shortening the time. According to the second embodiment, the coincidence count data coincidentally counted in the step (2) and the coincidence count data coincidentally counted in the step (3) according to the present invention are data acquired by one shooting, and the data acquired by one shooting is separated into coincidence count data for collection of the transmission data and coincidence count data for collection of the emission data so as to collect the transmission data in the step (2) and to collect the emission data in the step (3). According to the second embodiment, therefore, the coincidence counting circuit 6 separates the coincidence count data coincidentally counted in a state in which the subject M is present into data for collecting the transmission data and that for collecting the emission data. A specific separation method will be described later. The rotary drive mechanism 14 is configured to include a motor and the like that are not shown.

Figure 10:
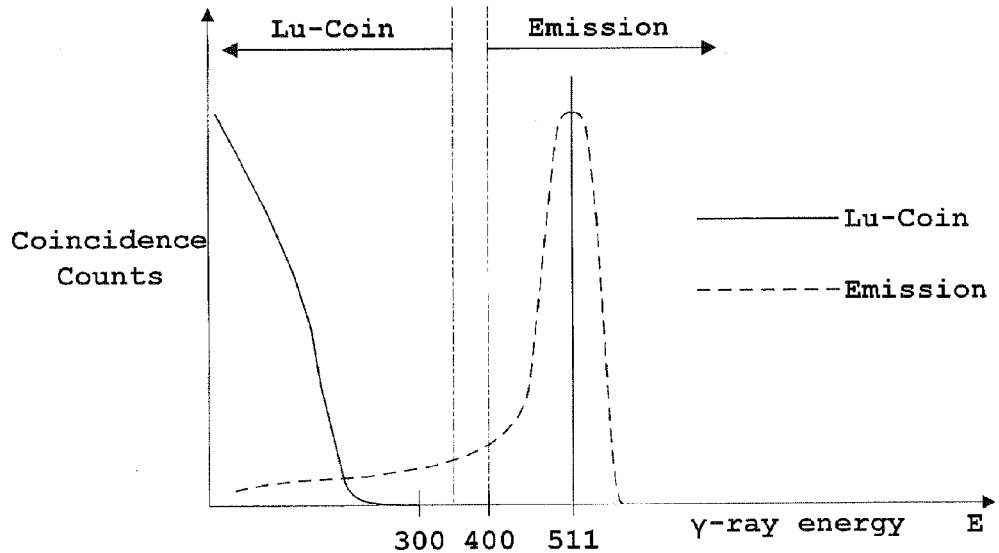
FIG. 10 is a pattern diagram for explaining separation based on energy.

A method of performing an arithmetic processing on each data (an arithmetic processing method) will next be described with reference to FIGS. 9 to 12. FIG. 9 is a flowchart showing a flow of a nuclear medicine diagnosis including the arithmetic processing method according to the second embodiment. FIG. 10 is a pattern diagram for explaining separation based on energy. FIG. 11 is a pattern diagram for explaining separation based on time difference. FIG. 12 is a pattern diagram for explaining separation based on space.

(Step S1) Collect Blank Data

Since step S1 is the same as that according to the first embodiment, it will not be described herein. Step S1 corresponds to the step (1) according to the present invention.

(Step T2) Collect Transmission Data and Emission Data

In the state in which the subject M is present, a radiopharmaceutical is administered into the subject M and in which a plurality of radiation detectors 1a each including a scintillator block 21 configured to contain a self-radioactivity element is arranged, γ rays emitted from the scintillator blocks 21 each configured to contain the self-radioactivity element are counted. At this time, some radiation detectors 1a each including the scintillator block 21 configured to contain the self-radioactivity element (that is, scintillators emitting γ rays) count some γ rays among the emitted γ rays. The other radiation detectors 1a count the other γ rays. By so counting, transmission data-emission data is collected while considering that the coincidence count data obtained by the coincidence counting circuit 6 is in a state in which γ-ray data from the radiopharmaceutical in the state in which the subject M is present (that is, emission data) and background data obtained by the self-radioactivity (that is, transmission data) are mixed ("E+T"). Step T2 corresponds to the steps (2) and (3) according to the present invention.

(Step T3) Separate Coincidence Count Data

As can be understood, the coincidence count data obtained in the step (2) according to the present invention and the coincidence count data obtained in the step (3) are the data acquired by one shooting. The coincidence counting circuit 6 separates the data into the coincidence count data for collecting the transmission data and that for collecting the emission data to be executed in the steps (2) and (3), respectively. Examples of the specific separation method include:

(A) Discrimination Method Based on Photonic Energy

The data acquired by one shooting is discriminated and separated based on photonic energy generated when γ rays are converted into photons during counting of the γ rays. If the data is to be collected by detecting γ rays of Lu-176 or the like different from the photonic energy, two types or more of energy windows (for example, an energy window for 350 KeV or lower and an energy window for 400 KeV or higher) are set. It is thereby possible to separate the coincidence count data into the emission data (see "Emission" in FIG. 10) by the energy window for 400 KeV or higher and the transmission data (see "Lu-Coin" in FIG. 10) by the energy window for 350 KeV or lower and to collect the emission data and the transmission data even after the radiopharmaceutical is administered into the subject M as shown in FIG. 10. As shown in a graph indicated by a dotted line shown in FIG. 10, if the photonic energy is equal to or lower than 350 KeV, spatter components in the radiation detectors 1a are often mixed into the emission data. However, it is not considered that the mixture provokes a serious problem for the method of extracting the profile.

(B) Discrimination Method Based on Time Difference Information (TOF: Time of Flight)

Figure 11A:
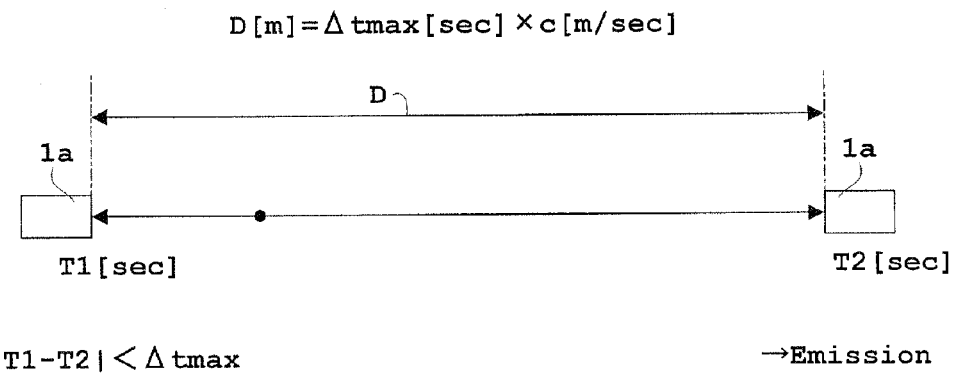
FIGS. 11A and 11B are pattern diagrams for explaining separation based on time difference.
Figure 11B:
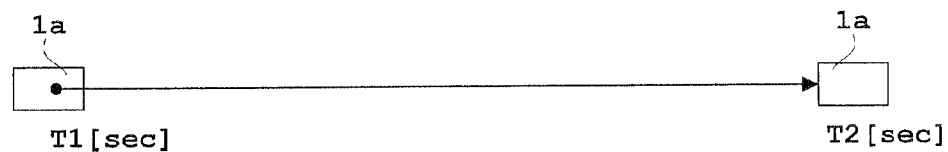

The data acquired by one shooting is discriminated and separated based on time difference information (TOF) during counting of the γ rays. If TOF when annihilation γ rays are coincidentally counted is accurately measured, a γ-ray radiation position (positron pair annihilation generation position) can be obtained from the TOF. A PET device based on this principle is referred to as "time difference information (or time of flight) (TOF) type PET". As shown in FIGS. 11A and 11B, it is assumed that a time difference of annihilation γ rays (annihilation photons) between two radiation detectors 1a used for coincidence counting is an absolute value |T1-T2| between T1 [sec] and T2 [sec], a γ-ray (photon) speed is c [cm/sec], a distance between the two radiation detectors 1a used for coincidence counting is D [m], and that a (time) range decided by the distance between the two radiation detectors 1a is Δtmax [sec]. In this case, the distance D is represented as D [m]=Δtmax [sec]×c [cm/sec]. As shown in FIG. 11A, the time difference |T1-T2| of annihilation photons generated from the subject M between the two radiation detectors 1a falls within the range (see |T1-T2|<Δtmax). Therefore, data can be discriminated as the emission data (see "Emission" in FIG. 11A). On the other hand, the time difference |T1-T2| of annihilation photons generated from within the radiation detectors 1a (that is, emitted by the self-radioactivity) is the time difference (Δtmax−Diff≦|T1-T2|≦Δtmax+Diff) surely decided by the distance between the two radiation detectors 1a as shown in FIG. 11B. Therefore, data can be discriminated as the transmission data (see "Lu-Coin" in FIG. 11B). In this way, two types of γ rays can be discriminated from each other based on this time difference and generation position information. While a random coincidence count is included in each of the emission-data related count and the transmission-data related count, the random coincidence count can be removed by such a method of delay coincidence counting.

(C) Discrimination Method Based on Spatial Information

As shown in FIG. 8B, if the radiation detector 1a configured to contain the self-radioactivity element (see a hatched part indicated by positive slopes in FIG. 8B) is combined with the radiation detectors 1a each configured not to contain the self-radioactivity element (for example, configured to contain GSO), the data acquired by one shooting is discriminated and separated based on spatial information obtained by each of the combinations of the radiation detectors 1a. FIGS. 12A to 12D show lines (LORs: Lines of Response) connecting the radiation detectors 1a used for coincidence counting in a structure shown in FIG. 8B by chain lines.

Figure 12A:
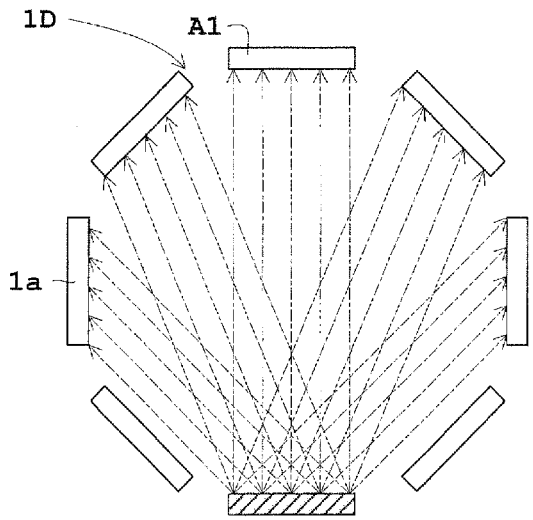
FIGS. 12A to 12D are pattern diagrams for explaining separation based on space.

As shown in FIG. 12A, on LORs related to γ rays emitted from the radiation detector 1a configured to contain the self-radioactivity element (see a hatched part indicated by positive slopes in FIG. 12A), if attention is paid to, for example, the radiation detector 1a denoted by a reference symbol A1, transmission data (T) based on the γ rays emitted from the self-radioactivity element and emission data (R) based on the γ rays emitted from the subject M are mixed (see "E+T" in FIG. 12A). Accordingly, as shown in FIG. 12B, by coincidentally counting γ rays while the rotary drive mechanism 14 (see FIG. 7) drives the ring radiation detection mechanisms 1D to rotate around the body axis of the subject M, the emission data and the transmission data are collected.

Figure 12C:
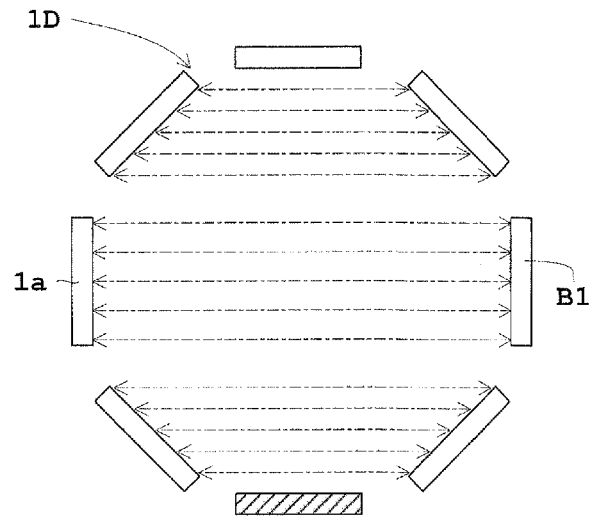

As shown in FIG. 12C, if LORs related to γ rays emitted from the subject M are present along the radiation detector 1a configured to contain the self-radioactivity element (see a hatched part indicated by positive slopes in FIG. 12C), the γ rays emitted from the self-radioactivity element are not counted as data obtained from respective projection directions (while paying attention to, for example, the radiation detector 1a denoted by a reference symbol B1) and the transmission data is not included in the data obtained from respective projection directions. Therefore, the data obtained from respective projection directions is only the emission data (R) (see "E" in FIG. 12C). Accordingly, as shown in FIG. 12D, by coincidentally counting γ rays while the rotary drive mechanism 14 (see FIG. 7) drives the ring radiation detection mechanisms 1D to rotate around the body axis of the subject M, only the emission data is collected.

Figure 12B:
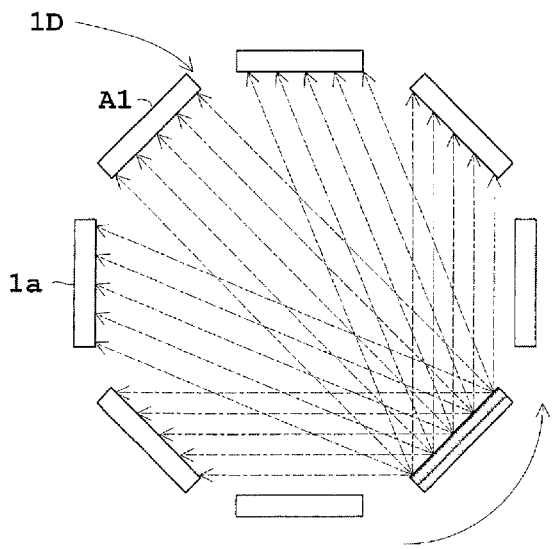
Figure 12D:
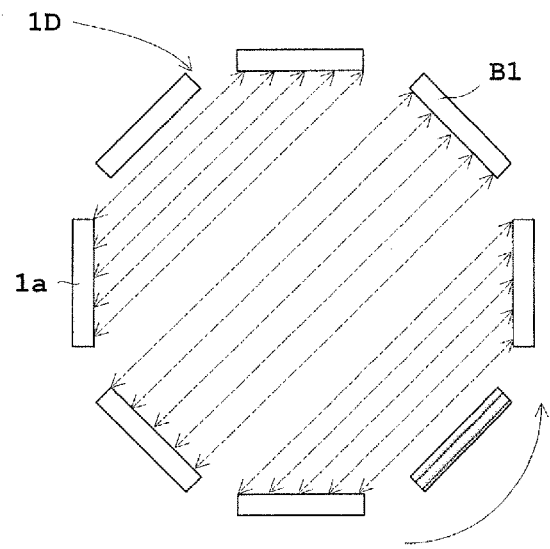

On the LORs shown in FIGS. 12A and 12B, the emission data and the transmission data are mixed. On the LORs shown in FIGS. 12C and 12D, only the emission data is collected. Therefore, the emission data can be separated from the transmission data by subtracting only the emission data from the mixture data of the emission data and the transmission data.

(Step S4) Obtain Count Ratio Sinogram

Since step S4 is the same as that according to the first embodiment, it will not be described herein.

(Step S5) Obtain Profile Sinogram

Since step S5 is the same as that according to the first embodiment, it will not be described herein.

(Step S6) Extract Profile Image

Since step S6 is the same as that according to the first embodiment, it will not be described herein.

(Step S7) Create Absorption Coefficient Map

Since step S7 is the same as that according to the first embodiment, it will not be described herein. Steps S4 to S7 correspond to the step (4) according to the present invention.

(Step S8) Conduct Absorption Correction and Reconstruction

Since step S8 is the same as that according to the first embodiment, it will not be described herein. Step S8 corresponds to a step (5) according to the present invention.

The PET device according to the second embodiment configured as stated above can conduct stable absorption correction by rather using the background data obtained by the element emitting a plurality of radiant rays simultaneously for the absorption-corrected data similarly to the first embodiment. Furthermore, according to the second embodiment, similarly to the first embodiment, the absorption correction is conducted without providing the external radiant source. It is, therefore, advantageously possible to make the radiation detectors 1a proximate to the subject M, downsize the PET device as shown in the PET device shown in FIG. 7 and improve device sensitivity.

In the second embodiment, if the data is discriminated based on the spatial information, radiant rays are coincidentally counted while the rotary drive mechanism 14 drives the ring radiation detection mechanisms 1D each configured so that the radiation detectors 1a each configured to contain the element emitting a plurality of radiant rays simultaneously (that is, the self-radioactivity element such as Lu-176) and the radiation detectors 1a each configured not to contain the self-radioactivity element are arranged in the ring shape to surround the body axis of the subject M to rotate around the body axis of the subject M. By doing so, among the LORs that are lines connecting the two radiation detectors 1a used for coincidence counting, spatial information on the space in which the transmission data based on the γ rays emitted from the radiation detectors 1a each configured to contain the self-radioactivity element and the emission data on the LORs related to the radiation detectors 1a configured to contain the self-radioactivity element and based on the γ rays emitted from the subject M are mixed up is collected. Further, spatial information on the space on the LORs related only to the radiation detectors 1a each configured not to contain the self-radioactivity element and only on the emission data based on the γ rays emitted from the subject M is collected. Moreover, the collected spatial information only on the emission data is subtracted from the collected spatial information in which the emission data and the transmission data are mixed up. It is thereby possible to separate the data acquired by one shooting (in step T2 of collecting the transmission data and the emission data) for coincidentally counting the radiant rays while the ring radiation detection mechanisms 1D are driven to rotate around the body axis of the subject M.

Third Embodiment

A third embodiment according to the present invention will be described below with reference to the drawings.

Figure 13:
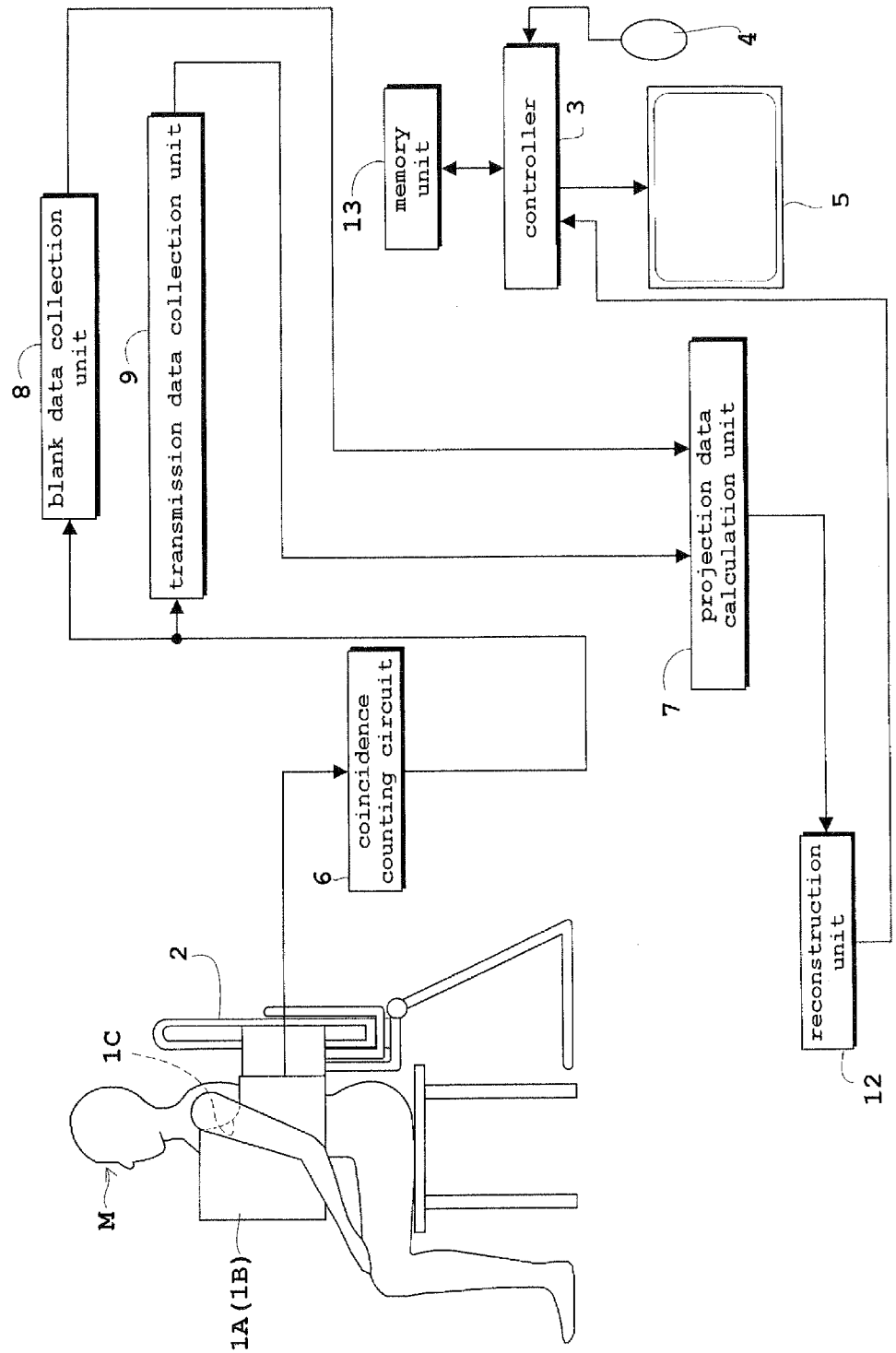
FIG. 13 is a side view and a block diagram of a PET mammography device according to a third embodiment.
Figure 14:
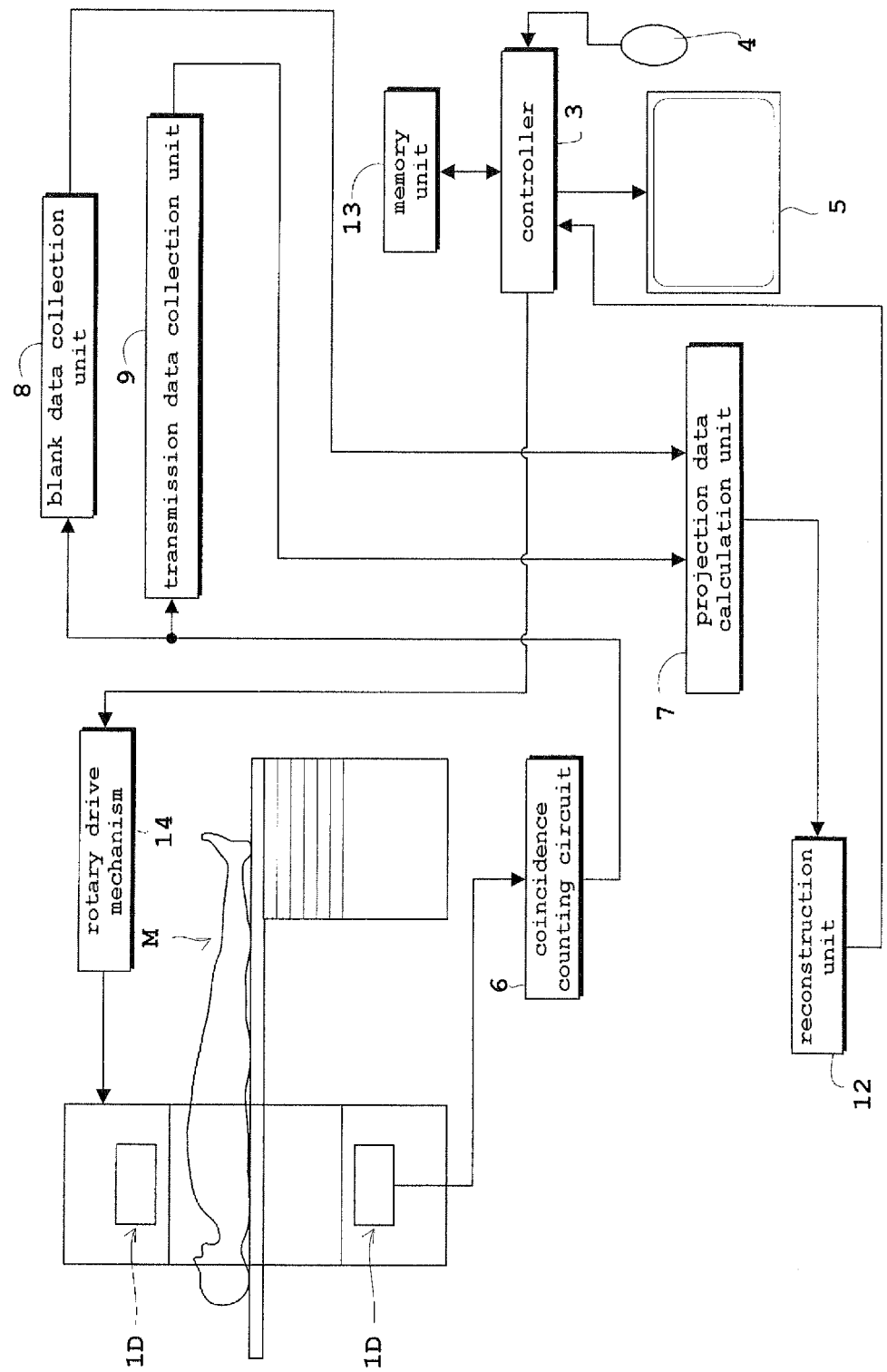
FIG. 14 is a side view and a block diagram of a PET device according to the third embodiment.

FIG. 13 is a side view and a block diagram of a PET mammography device according to the third embodiment. FIG. 14 is a side view and a block diagram of a PET device according to the third embodiment. In the third embodiment, similarly to the preceding first and second embodiments, a form tomography diagnosis device will be described while taking the PET mammography device and the PET device as examples. In the third embodiment, an instance in which the present invention is applied to a PET mammography device similar to that according to the first embodiment and an instance in which the present invention is applied to a PET device including ring radiation detectors 1D similar to that according to the second embodiment will be described with reference to FIG. 13 showing the side view and the block diagram of the PET mammography device and to FIG. 14 showing the side view and the block diagram of the PET device, respectively.

The third embodiment differs from the first and second embodiments in that form tomograms not only for nuclear medicine diagnosis but also for form tomograms are obtained. Since constituent elements of the PET device according to the third embodiment are similar in configuration to those of the PET mammography device and those of the PET device according to the first and second embodiments except for a projection data calculation unit 7, only the projection data calculation unit 7 will be described herein.

In the third embodiment, the projection data calculation unit 7 acquires perspective images of a subject M based on blank data collected by a blank data collection unit 8 and transmission data collected by a transmission data collection unit 9. That is, in the third embodiment, background data obtained by self-radioactivity is used not for absorption correction differently from the first and second embodiments but for the perspective images or form tomograms. In the third embodiment, a transmission factor of the subject M can be obtained as a perspective image for every pixel from a ratio of the transmission data to the blank data for every pixel. A reconstruction unit 12 reconstructs perspective images, thereby acquiring form tomograms (absorption coefficient distribution images) of the subject M. The projection data calculation unit 7 corresponds to a perspective image acquisition unit according to the present invention. The reconstruction unit 12 corresponds to a form tomogram acquisition unit according to the present invention.

A method of performing an arithmetic processing (an arithmetic processing method) on each data will next be described with reference to FIG. 15. FIG. 15 is a flowchart showing a flow of a form tomography diagnosis including the arithmetic processing method according to the third embodiment.

(Step S1) Collect Blank Data

Since step S1 is the same as that according to the first and second embodiments, it will not be described herein. Step S1 corresponds to the step (1) according to the present invention.

(Step S2) Collect Transmission Data

Since step S2 is the same as that according to the first embodiment, it will not be described herein. Step S2 corresponds to the step (2) according to the present invention.

(Step U3) Acquire Perspective Views

The projection calculation unit 7 obtains the transmission factor of the subject M for every pixel as a perspective image from the ratio of the blank data collected by the blank data collection unit 8 in step S1 to the transmission data collected by the transmission data collection unit 9. Step U3 corresponds to a step (6) according to the present invention.

(Step U4) Reconstruct Perspective Views

The reconstruction unit 12 reconstructs the perspective images (that is, projection data) obtained by the projection data calculation unit 7 in step U3, thereby obtaining tomograms as form tomograms. No considerations are given to as to whether or not the data is used for the absorption correction as done in the first and second embodiments.

In the PET device according to the third embodiment configured as stated above, degrees of absorption (including transmission) of γ rays depending on presence and absence of the subject M can be recognized based on the blank data collected by the blank data collection unit 8 and the transmission data collected by the transmission data collection unit 9, and the projection data calculation unit 7 can acquire the perspective images of the subject M. Furthermore, the reconstruction unit 12 reconstructs the perspective images and obtains the form tomograms. In this way, by rather using the background data obtained by the element (self-radioactivity element) emitting a plurality of radiant rays simultaneously, form tomograms that can be used for a processing and a diagnosis of nuclear medicine data or for grasping form information can be acquired. An applicable range of this acquired form information is not limited to the nuclear medicine diagnosis.

The present invention is not limited to the above-stated embodiments but various changes and modifications can be made of the invention as follows.

(1) In each of the first to third embodiments, the external radiant source is not provided. However, the present invention may be applied to a device of a type, such as a PET-CT device configured to include a PET device and an X-ray CT device, for irradiating radiant rays (X-ray in case of the X-ray CT device) different in type from the radiopharmaceutical from externally of the subject M or to a device of a type for irradiating radiant rays same in type as the radiopharmaceutical from externally of the subject M. Examples of the external radiant ray mentioned herein include not only an external radiant source irradiating radiant rays same in type as the radiopharmaceutical but also an external radiant source (an X-ray irradiation unit in case of the X-ray CT device) irradiating radiant rays (X rays in case of the X-ray CT device) different in type from the radiopharmaceutical from externally of the subject M.

(2) In the first and second embodiments, the profile of the subject M is extracted based on the ratio of the transmission data to the blank data when extracting the profile of the subject M and creating the absorption coefficient map of the subject M. Alternatively, the profile of the subject M can be extracted based on a difference between the transmission data and the blank data. Alternatively, the profile of the subject M can be extracted only using the transmission data without blank data. Furthermore, the absorption coefficient map is used solely without combination with a conventional profile extraction technique. Alternatively, the absorption coefficient map may be combined with the conventional profile extraction technique so as to improve profile extraction accuracy. For example, the profile of the subject M may be extracted using emission data as well as the transmission data and the blank data. In another alternative, the emission data may be compared with the absorption-corrected data obtained from the ratio of the transmission data to the blank data (or difference therebetween), one of the data may be selected as more accurate data, and the absorption correction may be conducted using the selected data.

(3) In the first and second embodiments stated above, the absorption-corrected data is obtained by extracting the profile of the subject M based on the ratio of the transmission data to the blank data and creating the absorption coefficient map of the subject M. Alternatively, the absorption-corrected data can be obtained by calculating an inverse of the transmission factor of the subject M obtained based on the ratio of the transmission data to the blank data without creating the absorption coefficient map.

(4) In the first and second embodiments, the absorption coefficient map is a map on the assumption that the interior of the subject M is regarded as a uniform absorber. Alternatively, the absorption coefficient map may be a map on the assumption that the interior of the subject M is regarded as an absorber constituted by a plurality of absorption coefficient segments. In this alternative, the profile of the subject M and internal form information that forms basis for the absorption coefficient segments are extracted from the ratio of the transmission data to the blank data (or difference therebetween). Furthermore, if the profile of the subject M is extracted only from the transmission data and the absorption coefficient map is created, the profile of the subject and the internal form information that forms basis for the absorption coefficient segments are extracted only from the transmission data. In this way, in the modification (4), a more accurate absorption coefficient map can be created according to an actual subject and more accurate absorption correction can be thereby conducted.

The present invention may be embodied in other specific forms without departing from the spirit or essential attributes thereof and, accordingly, reference should be made to the appended claims, rather than to the foregoing specification, as indicating the scope of the invention.

What is claimed is:

1. A nuclear medicine diagnosis device for obtaining nuclear medicine data on a subject injected with a radiopharmaceutical based on radiant rays generated from the subject, comprising:
    a radiation detection unit configured to contain an element emitting a plurality of radiant rays simultaneously;
    a blank data collection unit collecting coincidence count data as blank data, the coincidence count data being coincidentally counted by causing the radiation detection unit configured to contain the element to count some of the radiant rays emitted from the element contained in the radiation detection unit and causing another radiation detection unit to count other radiant rays in a state in which the subject is absent;
    a transmission data collection unit collecting coincident count data as transmission data, the coincidence count data being coincidentally counted by causing the radiation detection unit configured to contain the element to count some of the radiant rays emitted from the element contained in the radiation detection unit and another radiation detection unit to count other radiant rays in a state in which the subject is present;
    an emission data collection unit collecting coincidence count data as emission data, the coincidence count data being coincidentally counted by causing the radiation detection unit to count the radiant rays generated from the subject injected with the radiopharmaceutical;
    an absorption-corrected data calculation unit calculating absorption-corrected data on the subject based on at least one of the blank data collected by the blank data collection unit and the transmission data collected by the transmission data collection unit; and
    an absorption correction unit absorption-correcting the emission data collected by the emission data collection unit using the absorption-corrected data, and finally obtaining the absorption-corrected emission data as the nuclear medicine data.

2. The nuclear medicine diagnosis device according to claim 1,
    wherein the absorption-corrected data calculation unit calculates the absorption-corrected data by extracting a profile of the subject only using the transmission data and creating an absorption coefficient map of the subject.

3. The nuclear medicine diagnosis device according to claim 1,
    wherein the absorption-corrected data calculation unit calculates the absorption-corrected data by extracting a profile of the subject using the transmission data and the blank data and creating an absorption coefficient map of the subject.

4. The nuclear medicine diagnosis device according to claim 3, wherein the absorption-corrected data calculation unit extracts the profile of the subject based on a ratio of the transmission data to the blank data or a difference between the transmission data and the blank data.

5. The nuclear medicine diagnosis device according to claim 2, wherein the absorption coefficient map is a map on assumption that an interior of the subject is regarded as an absorber.

6. The nuclear medicine diagnosis device according to claim 3, wherein the absorption coefficient map is a map on assumption that an interior of the subject is regarded as an absorber.

7. The nuclear medicine diagnosis device according to claim 2, wherein the absorption coefficient map is a map on assumption that an interior of the subject is regarded as an absorber constituted by a plurality of absorption coefficient segments, and
the absorption-corrected data calculation unit extracts the profile of the subject and internal form information that form basis for the absorption coefficient segments only using the transmission data.

8. The nuclear medicine diagnosis device according to claim 3, wherein the absorption coefficient map is a map on assumption that an interior of the subject is regarded as an absorber constituted by a plurality of absorption coefficient segments, and
the absorption-corrected data calculation unit extracts the profile of the subject and internal form information that form basis for the absorption coefficient segments using the transmission data and the blank data.

9. The nuclear medicine diagnosis device according to claim 3, wherein the absorption-corrected data calculation unit calculates the absorption-corrected data by extracting the profile of the subject using the emission data as well as the transmission data and the blank data and creating the absorption coefficient map of the subject.

10. The nuclear medicine diagnosis device according to claim 1, wherein the absorption-corrected data calculation unit calculates the absorption-corrected data by calculating an inverse of a transmission factor of the subject obtained based on a ratio of the transmission data to the blank data.

11. The nuclear medicine diagnosis device according to claim 1, wherein the coincidence count data coincidentally counted by the transmission data collection unit differs from the coincidence count data coincidentally counted by the emission data collection unit.

12. The nuclear medicine diagnosis device according to claim 1, wherein the coincidence count data coincidentally counted by the transmission data collection unit and the coincidence count data coincidentally counted by the emission data collection unit are data acquired by one shooting, and
the data acquired by one shooting is separated into coincidence count data for collection of the transmission data and coincidence count data for collection of the emission data so as to cause the transmission data collection unit to collect the transmission data and the emission data collection unit to collect the emission data.

13. The nuclear medicine diagnosis device according to claim 12, wherein the data acquired by one shooting is separated based on an energy from the radiant rays during counting of the radiant rays.

14. The nuclear medicine diagnosis device according to claim 12, wherein the data acquired by one shooting is separated based on time difference information during counting of the radiant rays.

15. The nuclear medicine diagnosis device according to claim 12, wherein the data acquired by one shooting is separated based on spatial information obtained by each of the radiation detection unit configured to contain the element and a radiation detection unit configured not to contain the element if the radiation detection unit configured to contain the element is combined with the radiation detection unit configured not to contain the element.

16. The nuclear medicine diagnosis device according to claim 15, comprising:
a ring radiation detection mechanism configured to arrange the radiation detection unit configured to contain the element and the radiation detection unit configured not to contain the element into a ring shape to surround a body axis of the subject; and
a rotary drive mechanism driving the ring radiation detection mechanism to rotate around the body axis of the subject,
wherein by coincidentally counting the radiant rays while causing the rotary drive mechanism to drive the ring radiation detection mechanism to rotate around the body axis of the subject, the spatial information in which the transmission data based on the radiant rays emitted from the radiation detection unit configured to contain the element on LORs connecting paired radiation detection units used for coincidence counting and the emission data based on the radiant rays generated from the subject injected with the radiopharmaceutical on one of the LORs related to the radiation detection unit configured to contain the element are mixed up, the LORs being abbreviation of line of response,
the spatial information only on the emission data based on the radiant rays generated from the subject injected with the radiopharmaceutical on one of the LORs related only to the radiation detection unit configured not to contain the element among the LORs is collected, and
the spatial information only on the collected emission data is subtracted from the spatial information in which the collected emission data and the collected transmission data are mixed up, thereby separating the data acquired by one shooting for coincidence counting of the radiant rays while causing the rotary drive mechanism to drive the ring radiation detection mechanism to rotate about the body axis of the subject.

17. A form tomography diagnosis device obtaining a form tomogram of a subject injected with a radiopharmaceutical based on radiant rays generated from the subject, comprising:
a radiation detection unit configured to contain an element emitting a plurality of radiant rays simultaneously;

a blank data collection unit collecting coincidence count data as blank data, the coincidence count data being coincidentally counted by causing the radiation detection unit configured to contain the element to count some of the radiant rays emitted from the element contained in the radiation detection unit and causing another radiation detection unit to count other radiant rays in a state in which the subject is absent;

a transmission data collection unit collecting coincident count data as transmission data, the coincidence count data being coincidentally counted by causing the radiation detection unit configured to contain the element to count some of the radiant rays emitted from the element contained in the radiation detection unit and another radiation detection unit to count other radiant rays in a state in which the subject is present;

a perspective image acquisition unit acquiring a perspective image of the subject based on the blank data collected by the blank data collection unit and the transmission data collected by the transmission data collection unit; and a form tomogram acquisition unit reconstructing the perspective image and acquiring the form tomogram of the subject.

18. A nuclear medicine data arithmetic processing method of performing an arithmetic processing on nuclear medicine data on a subject injected with a radiopharmaceutical based on radiant rays generated from the subject, comprising the steps of:

(1) collecting coincidence count data as blank data, the coincidence count data being coincidentally counted by causing a radiation detection unit configured to contain an element emitting a plurality of radiant rays simultaneously to count some of the radiant rays emitted from the element contained in the radiation detection unit and causing another radiation detection unit to count other radiant rays in a state in which the subject is absent;

(2) collecting coincident count data as transmission data, the coincidence count data being coincidentally counted by causing the radiation detection unit configured to contain the element to count some of the radiant rays emitted from the element contained in the radiation detection unit and another radiation detection unit to count other radiant rays in a state in which the subject is present;

(3) collecting coincidence count data as emission data, the coincidence count data being coincidentally counted by causing the radiation detection unit to count the radiant rays generated from the subject injected with the radiopharmaceutical;

(4) calculating absorption-corrected data on the subject based on at least one of the blank data and the transmission data;

(5) absorption-correcting the emission data using the absorption-corrected data; and performing the arithmetic processing including the steps (1) to (5) for finally obtaining the absorption-corrected emission data as the nuclear medicine data.

19. The nuclear medicine data arithmetic processing method according to claim 18,
wherein in the step (4), the absorption-corrected data is calculated by extracting a profile of the subject only using the transmission data and creating an absorption coefficient map of the subject.

20. The nuclear medicine data arithmetic processing method according to claim 18,
wherein in the step (4), the absorption-corrected data is calculated by extracting a profile of the subject using the transmission data and the blank data and creating an absorption coefficient map of the subject.

21. The nuclear medicine data arithmetic processing method according to claim 20,
wherein in the step (4), the profile of the subject is extracted based on a ratio of the transmission data to the blank data or a difference between the transmission data and the blank data.

22. The nuclear medicine data arithmetic processing method according to claim 19,
wherein the absorption coefficient map is a map on assumption that an interior of the subject is regarded as an absorber.

23. The nuclear medicine data arithmetic processing method according to claim 20,
wherein the absorption coefficient map is a map on assumption that an interior of the subject is regarded as an absorber.

24. The nuclear medicine data arithmetic processing method according to claim 19,
wherein the absorption coefficient map is a map on assumption that an interior of the subject is regarded as an absorber constituted by a plurality of absorption coefficient segments, and
in the step (4), the profile of the subject and internal form information that form basis for the absorption coefficient segments are extracted only using the transmission data.

25. The nuclear medicine data arithmetic processing method according to claim 20,
wherein the absorption coefficient map is a map on assumption that an interior of the subject is regarded as an absorber constituted by a plurality of absorption coefficient segments, and
in the step (4), the profile of the subject and internal form information that form basis for the absorption coefficient segments are extracted using the transmission data and the blank data.

26. The nuclear medicine data arithmetic processing method according to claim 20,
wherein in the step (4), the absorption-corrected data is calculated by extracting the profile of the subject using the emission data as well as the transmission data and the blank data and creating the absorption coefficient map of the subject.

27. The nuclear medicine data arithmetic processing method according to claim 18,
wherein in the step (4), the absorption-corrected data is calculated by calculating an inverse of a transmission factor of the subject obtained based on a ratio of the transmission data to the blank data.

28. The nuclear medicine data arithmetic processing method according to claim 18,
wherein the coincidence count data coincidentally counted in the step (2) differs from the coincidence count data coincidentally counted in the step (3).

29. The nuclear medicine data arithmetic processing method according to claim 18,
wherein the coincidence count data coincidentally counted in the step (2) and the coincidence count data coincidentally counted in the step (3) are data acquired by one shooting, and
the data acquired by one shooting is separated into coincidence count data for collection of the transmission data and coincidence count data for collection of the emission data so as to collect the transmission data in the step (2) and to collect the emission data in the step (3).

30. The nuclear medicine data arithmetic processing method according to claim 29,
wherein the data acquired by one shooting is separated based on an energy from the radiant rays during counting of the radiant rays.

31. The nuclear medicine data arithmetic processing method according to claim 29,
wherein the data acquired by one shooting is separated based on time difference information during counting of the radiant rays.

32. The nuclear medicine data arithmetic processing method according to claim 29,
wherein the data acquired by one shooting is separated based on spatial information obtained by each of the radiation detection unit configured to contain the element and a radiation detection unit configured not to contain the element if the radiation detection unit configured to contain the element is combined with the radiation detection unit configured not to contain the element.

33. The nuclear medicine data arithmetic processing method according to claim 32, comprising the steps of:
by coincidentally counting the radiant rays while driving a ring radiation detection mechanism configured to arrange the radiation detection unit configured to contain the element and the radiation detection unit configured not to contain the element into a ring shape to surround a body axis of the subject to rotate around the body axis of the subject, collecting the spatial information in which the transmission data based on the radiant rays emitted from the radiation detection unit configured to contain the element on LORs connecting paired radiation detection units used for coincidence counting and the emission data based on the radiant rays generated from the subject injected with the radiopharmaceutical on one of the LORs related to the radiation detection unit configured to contain the element are mixed up, the LORs being abbreviation of lines of response; and collecting the spatial information only on the emission data based on the radiant rays generated from the subject injected with the radiopharmaceutical on one of the LORs related only to the radiation detection unit configured not to contain the element among the LORs,
wherein the spatial information only on the collected emission data is subtracted from the spatial information in which the collected emission data and the collected transmission data are mixed up, thereby separating the data acquired by one shooting for coincidence counting of the radiant rays while causing the rotary drive mechanism to drive the ring radiation detection mechanism to rotate about the body axis of the subject.

34. A form tomogram arithmetic processing method of performing an arithmetic processing on a form tomogram of a subject injected with a radiopharmaceutical based on radiant rays generated from the subject, comprising the steps of:
(1) collecting coincidence count data as blank data, the coincidence count data being coincidentally counted by causing a radiation detection unit configured to contain an element emitting a plurality of radiant rays simultaneously to count some of the radiant rays emitted from the element contained in the radiation detection unit and causing another radiation detection unit to count other radiant rays in a state in which the subject is absent;
(2) collecting coincident count data as transmission data, the coincidence count data being coincidentally counted by causing the radiation detection unit configured to contain the element to count some of the radiant rays emitted from the element contained in the radiation detection unit and another radiation detection unit to count other radiant rays in a state in which the subject is present;
(6) acquiring a perspective image of the subject based on the blank data and the transmission data; and
performing the arithmetic processing including the steps (1), (2), and (6) for reconstructing the perspective image and obtaining the form tomogram of the subject.

* * * * *